(12) United States Patent
Reymond et al.

(10) Patent No.: US 8,741,593 B2
(45) Date of Patent: Jun. 3, 2014

(54) METHOD FOR RELEASING A PRODUCT COMPRISING CHEMICAL OXIDATION, METHOD FOR DETECTING SAID PRODUCT AND USES THEREOF

(75) Inventors: Jean-Louis Reymond, Berne (CH); Denis Wahler, Berne (CH); Frabrizzio Badalassi, Venturina (IT); Hong-Khanh Nguyen, Nimes (FR)

(73) Assignee: Proteus, Nimes (FR)

( * ) Notice: Subject to any disclaimer, the term of this patent is extended or adjusted under 35 U.S.C. 154(b) by 1070 days.

(21) Appl. No.: 11/601,649

(22) Filed: Nov. 20, 2006

(65) Prior Publication Data

US 2007/0099257 A1  May 3, 2007

Related U.S. Application Data

(63) Continuation of application No. 10/307,490, filed on Dec. 2, 2002, now abandoned, which is a continuation of application No. PCT/FR01/01686, filed on May 30, 2001.

(30) Foreign Application Priority Data

May 30, 2000 (FR) ..................................... 00/06952
Oct. 20, 2000 (FR) ..................................... 00/13487

(51) Int. Cl.
*C12Q 1/26* (2006.01)
*C12Q 1/00* (2006.01)
*G01N 33/00* (2006.01)
*C12P 13/00* (2006.01)
*C12P 11/00* (2006.01)
*C12P 7/00* (2006.01)
*C12P 7/24* (2006.01)
*C12P 7/26* (2006.01)
*C12N 13/00* (2006.01)

(52) U.S. Cl.
USPC ................ 435/25; 435/4; 435/7.95; 435/128; 435/130; 435/132; 435/147; 435/148; 435/173.2

(58) Field of Classification Search
None
See application file for complete search history.

(56) References Cited

U.S. PATENT DOCUMENTS

| | | | |
|---|---|---|---|
| 4,277,561 A | 7/1981 | Monget et al. | |
| 4,603,108 A | 7/1986 | Bascomb | |
| 4,778,757 A | 10/1988 | Teshima et al. | |
| 5,122,602 A | 6/1992 | Corey et al. | |
| 5,162,203 A | 11/1992 | Vallee | |
| 5,196,312 A | 3/1993 | Miike et al. | |
| 5,583,217 A | 12/1996 | Quante et al. | |
| 5,846,754 A | 12/1998 | Pugia et al. | |
| 6,455,268 B1 | 9/2002 | Jarnigan et al. | |
| 7,238,483 B2 * | 7/2007 | Reymond et al. .................. 435/6 | |

FOREIGN PATENT DOCUMENTS

| | | |
|---|---|---|
| EP | 0 317 243 | 5/1989 |
| EP | 0 317 243 A2 | 5/1989 |
| EP | 0 451 775 A1 | 10/1991 |
| EP | 0 796 854 A1 | 9/1997 |
| EP | 0 810 290 | 12/1997 |
| WO | 01/36662 | 5/2001 |
| WO | 01/60986 | 8/2001 |
| WO | 01/61041 | 8/2001 |
| WO | 01/92563 A2 | 12/2001 |

OTHER PUBLICATIONS

Wahler, et al, "Enzyme Fingerprints by Fluorogenic and Chromogenic Substrate Arrays" Angew. Chem. Int. Ed., 2001, 40(23), pp. 4457-4460.*
Holzwarth et al., IR-thermographische erkennung katalytischer aktivitat in kombinatorischen bibliotheken heterogener katalysatoren, Angew. Chem. 1998, 110, Nr. 19, pp. 2788-2792.
Reetz et al., Eine methode zum high-throughput-screening von enantioselektiven katalysatoren, Angew. Chem. 1999, 111, Nr. 12, pp. 1872-1875.
Reetz et al., IR-Thermographie-Screening von thermoneutralen oder endothermen reaktionen: die ringschluss-Olefin-Metathese, Angew. Chem. 2000, 112, Nr. 7, pp. 1294-1298.
Reetz et al., IR-Thermographic screening of thermoneutral or endothermic transformations: The ring-closing olefin metathesis reaction, Angew. Chew. Int. Ed. 2000, 39, No. 7, pp. 1236-1239.
Harris, Jennifer et al., "Rapid and general profiling of protease specificity by using combinatorial fluorogenic substrate libraries", PNAS (Jul. 5, 2000), pp. 7754-7759, vol. 97, No. 14.
El-Kommos et al., Spectrophotometric Determination of some catecholamine drugs using metaperiodate, J. Assoc. Off. Anal. Chem. (vol. 73, No. 4, 1990), pp. 516-520.
Firestine et al., Using an araC-based three-hybrid system to detect biocatalysts in vivo, Nature Biotecnology, vol. 18, May 2000, pp. 544-547.

(Continued)

*Primary Examiner* — Chris R Tate
*Assistant Examiner* — Aaron J Kosar
(74) *Attorney, Agent, or Firm* — Hunton & Williams LLP

(57) ABSTRACT

This invention has as its object a method for releasing a product by subjecting a compound of Formula (II'): $R'_7R'_8(HX)C_1-C_2(YH)R'_9R'_{10}$ to a chemical oxidation that cleaves the bond $C_1-C_2$ to obtain the product. In the compound of Formula (II'): $R'_7$ to $R'_{10}$, which are identical or different, correspond to a hydrogen atom, a substituted or unsubstituted alkyl group, or a substituted or unsubstituted functional group; X and Y, which are identical or different, are an oxygen atom, a sulfur atom, or an amine of Formula $-NR_{11}R_{12}$, wherein $R_{11}$ is a hydrogen atom, an alkyl group, or a substituted or unsubstituted aryl group, and $R_{12}$ is not a hydrogen atom. The invention also has as its object a method for releasing a product that comprises, before the chemical oxidation stage, a first step for preparing the compound of Formula (II'). The released product can be a volatile molecule or an active substance or else a specific product. The invention also relates to a method for detecting the released product as well as its applications, in particular for detecting catalytic or enzymatic activities.

17 Claims, 7 Drawing Sheets

(56) References Cited

OTHER PUBLICATIONS

Geymayer, et al., "A General Fluorogenic Assay for Catalysis using Antibody Sensors", Chem. Eur. J., vol. 5, No. 3, p. 1006-1012, 1999.
Carlon, et al., "Fluorogenic Polypropionate fragments for detecting Steroselective Algolases", Chem. Eur. J., vol. 6, No. 22, p. 4154-4162, 2000.
Gruninger-Leitch, et al., "Identification of beta-secretase-like activity using a mass spectrometry-based assay sysytem", Nature Biotechnology, vol. 18, p. 66-70, 2000.
Moris-Varas, et al., "Visualization of Enzume-Catalyzed Reactionsusing pH indicators: Rapid Screening of Hydrolase Libraries and Estimation of the Enantioselectivity", Bioorganic andMedicinal Chemistry, vol. 7, p. 2183-2188, 1999.
O'Brien, M. et al., "Enzymatic Profile of *Pseudomonas maltophilia*", Journal of Clinical Microbiology (Sep. 1982), pp. 417-421, vol. 16, No. 3.
Jourdain et al., A stereoselective flurogenic assay for aldolases: Detection of an anti-selective aldolase catalytic antibody, Tetrahedron Letters 39 (1998), pp. 9415-9418.
Taran et al., Competitive immunoassay (Cat-EIA), a helpful technique for catalytic antibody detection, Part I, Tetrahedron Letters 40 (1999), pp. 1887-1890.
Nogare, et al., "Determination of Acetaldehyde and Acetone by the Iodoform Reaction", Anal. Chem., vol. 23, p. 1473-1478, 1951.
F. Badalassi, D. WahleR, G. Klein, P. Crotti, J-L Reymond, "A Versatile Periodate-Coupled Flourogenic Assay for Hydrolytic Enzymes", Angewandte Chemie. International Edition, Nov. 17, 2000, pp. 4067-4070, vol. 39, Issue No. 22.
G-G. Chang, M-S Shiao, K-R Lee and J-J Wu, "Modification of human placental alkaline phosphatase by periodate -oxidized 1, N6 ethenoadenosine monophosphate", Biochem. J. (1990), pp. 683-90, vol. 273, Issue No. 3.
X-J. Chen, A. Archelas, R. Furstoss, Microbial Transformations. 27. The First Examples for Preparative-Scale Enantioselective or Diastereoselective Epoxide Hydrolyses Using Microorganisms. An Unequivocal Access to All Four Bisabolol Stereoisomers, J. Org. Chem. (1993), vol. 58 , pp. 5528-5532.
D. C. Demirjian, P. C. Shah, F. Moris-Varas, "Screening for Novel Enzymes", Topics in Current Chemistry (1999), vol. 200, pp. 1-29.
S. Hanessian, T. Takamoto, R. Massé, G. Patil, "Aminoglycoside antibiotics: chemical conversion of neomycin B, paromycin, and lividomycin B into bioactive pseudosaccharides". Can. J. Chem. (1978), vol. 56. Issue No. 11, pp. 1482-1491.
N. Jourdain, R. Pérez Carlón, J.-L. Reymond, "A Stereoselective Fluorogenic Assay for Aldolase: Detection of an Anti-Selective Aldolase Catalytic Antibody", Tetrahedron Letters, NL, (1998), vol. 39, pp. 9415-9418.
G. Klein, J.-L. Reymond, An Enantioselective Fluorometric Assay for Alcohol Dehydrogenases Using Albumin-Catalyzed beta-Elimination of Umbelliferone, Bioorganic & Medicinal Chemistry Letters, (1998), vol. 8, pp. 1113-1116.
G. Klein, J.-L. Reymond, "Enantioselection Fluorogenic Assay of Acetate Hydrolysis for Detecting Lipase Catalytic Antibodies", Helvetica Chimica Acta (1999), vol. 82, pp. 400-407.
J. Latip, T. G. Hartley, P. G. Waterman, "Lignans an coumarins metabolites from *Melicope hayesii*", Phytochemistry, May 1999, vol. 51, Issue No. 1, pp. 107-110.

B. List, C. F. Barbas, R. A. Lerner, "Aldol sensors for the rapid generation of tunable fluorescence by antibody catalysis", Proceedings of the National Academy of Sciences, USA, Dec. 22, 1998, vol. 95, Issue No. 26, pp. 15351-15355.
T. Matsumoto, Y. Takeda, E. Iwata, M. Sakamoto, T. Ishida, "Lipase-Catalyzed Hydrolysis of Some Racemic 1-Acetoxy-2-arylpropanes", Chemical & Pharmaceutical Bulletin, (1994), vol. 42, Issue No. 6, pp. 1191-1197.
K. L. Matta, C. F. Piskorz, J. J. Barlow, "A rapid synthesis of p-nitrophenyl 2-O-ÿ-L-fucopyranosyl-ÿ-D-galctopyranoside" Carbohydrate. Research, (1981), vol. 90, pp. 1 C1-C3.
J.G. Millar, A.E. Knudson, S. Mcelfresh, R.Gries, G. Gries, J.H. Davis). Bioorganic & Medicinal Chemistry, (1996), vol. 4, Issue No. 3, pp. 331-339.
M. T. Reetz, K.-E. Jaeger, "Superior Biocatalysts by Directed Evolution", Topics in Current Chemistry (1999), vol. 200, p. 31-57.
M. T. Reetz, G. Lohmer, R. Schwickardi, "A New Catalyst System for the Heck Reaction of Unreactive Aryl Halides", Angewandte Chemie. International Edition (1998), vol. 37, Issue No. 4, pp. 481-483.
C. A. Roeschlaub, N. L. Maidwell, M. R. Rezai, P. G. Sammes, "A fluorescent probe for the detection of NAD(P)H", Chemical Communications (1999), pp. 1637-1638.
T. Suzuki, "4,8-Dimethyldecanal: The Aggregation Pheromone of the Flour Beetles, *Tribolium castaneum* and *T. confusum*(Coleoptera: Tenebrionidae)", Agric. Biol. Chem., (1980), vol. 44, pp. 2519-2520.
C. A. G. M. Weijers, A. L. Botes, M. S. Van Dyk, J. A. M. De Bont, "Enantioselective hydroysis of unbranched aliphatic 1,2-epoxides by Rhodatorula glutinis", Tetrahedron Asymmetry (1998), vol. 9, pp. 467-473.
Ronald G. Harvey, et al., "Synthesis of the Tumorigenic 3,4-Dihydrodiol Metabolites of Dibenz[a, j]lanthracene and 7,14-Dimet hydibenz[a, j]anthracene", J. Med. Chem., vol. 31, p. 1308-1312, 1988.
G-G. Chang, M-S Shiao, K-R Lee and J-J Wu, "Modification of human placental alkaline phosphatase by periodate -oxidized 1, N6 ethenoadenosine monophosphate", Biochem. J. (1990), pp. 683-690, vol. 273, Issue No. 3.
G. Klein, J.-L. Reymond, An Enantioselective Fluorometric Assay for Alcohol Dehydrogenases Using Albumin-Catalyzed beta-Elimination of Umbelliferone, Bioorganic & Medicinal Chemistry Letters, GB, Oxford (1998), vol. 8, pp. 1113-1116.
J. Latip, T. G. Hartley, P. G. Waterman, "Lignans an coumarins metabolites from *Melicope hayesii*", Phytochemistry, Oxford, May 1999, vol. 51, Issue No. 1, pp. 107-110.
T. Matsumoto, Y. Takeda, E. Iwata, M. Sakamoto, T. Ishida, "Lipase-Catalyzed Hydrolysis of Some Racemic 1-Acetoxy-2-arylpropanes", Chemical & Pharmaceutical Bulletin, (1994), Tokyo, vol. 42, Issue No. 6, pp. 1191-1197.
K. L. Matta, C. F. Piskorz, J. J. Barlow, "A rapid synthesis of p-nitrophenyl 2-O-α-L-fucopyranosyl-β-D-galctopyranoside", Carbohydrate. Research, (1981), vol. 90, pp. C1-C3.
T. Suzuki, "4,8-Dimethyldecanal: The Aggregation Pheromone of the Flour Beetles, *Tribolium castaneum* and *T.confusum* (Coleoptera: Tenebrionidae)", Agric. Biol. Chem., (1980), vol. 44, pp. 2519-2520.

\* cited by examiner

METHOD FOR RELEASING A PRODUCT COMPRISING CHEMICAL OXIDATION, METHOD FOR DETECTING SAID PRODUCT AND USES THEREOF

CROSS REFERENCE TO RELATED APPLICATION

This patent application is a continuation of U.S. patent application Ser. No. 10/307,490, filed Dec. 2, 2002, which claims priority to French Application No. 00/06952, filed May 30, 2000, French Application No. 00/13487, filed Oct. 20, 2000, and PCT/FR01/01686, filed May 30, 2001, each of which is hereby incorporated by reference herein in its entirety.

BACKGROUND OF THE INVENTION (i) Field of the Invention

This present invention relates to a method for detecting a chemical transformation of a substrate such that said chemical transformation of this substrate releases a product, whereby said released product is then a detectable product.

The invention also relates to substrates that can be used in this method. The invention also relates to the use of this method in a process for detection and optionally quantification of a chemical transformation in a sample.

(ii) Description of Related Art

After reaction, many substrates release a product that provides an easily identifiable signal. It is possible to cite the well known examples of glycosides, esters and phosphates of phenols whose hydrolysis directly releases phenol, which is detected in general by its color (chromogenic substrate) or its fluorescence (fluorogenic substrate)) (D. C. Demirjian, P. C. Shah, F. Moris-Varas, Top. Curr. Chem. 1999, 200, 1; M. T. Reetz, K.-E. Jaeger, Top. Curr. Chem. 1999, 200, 31).

It is also possible to cite 2-methoxy-1-naphthalene methanol, whose oxidation provides fluorescent 2-methoxy-1-naphthaldehyde (B. L. Vallee, U.S. Pat. No. 5,162,203; B. List, C. F. Barbas, R. A. Lerner, Proc. Natl. Acad. Sci. USA 1998, 95, 15351 for use in aldolases).

These types of substrate have a major disadvantage: the chromogenic or fluorogenic phenol is a strongly activated group, which makes these substrates unstable and susceptible to non-specific reactions. In the case of 2-methoxy-1-naphthalene methanol, the problem is similar since the benzylic position is sensitive to non-specific oxidation.

A second class of substrate leads to the revealing of a product that is obtained after enzymatic secondary reaction and/or spontaneous secondary reaction. Several examples exist, such as penicillinase substrates (U.S. Pat. No. 5,583, 217), alcohol dehydrogenase (ADH) substrates (G. Klein, J.-L. Reymond, *Bioorg. Med. Chem. Lett.* 1998, 8, 1113) and aldolase substrates (N. Jourdain, R. Pérez Carlón, J.-L. Reymond, Tetrahedron Lett. 1998, 39, 9415).

It is also possible to note the existence of a substrate for measuring the NADH (C. A. Roeschlaub, N. L. Maidwell, M. R. Rezai, P. G. Sammes, Chem. Commun. 1999, 1637).

Finally, it is possible to cite substrates whose detected product of the secondary reaction is obtained by the action of the beta-galactosidase (K. L. Matta, C. F. Piskorz, J. J. Barlow, Carbohydr. Res. 1981, 90, C1-C3) or by ADH (G. Klein, J.-L. Reymond, Helv. Chim. Acta 1999, 82, 400).

This second class of substrate is more stable. This second class of substrate, however, is limited to particular uses, because the fact of using an enzyme for the secondary reaction represents a drawback in terms of cost and flexibility.

The research work carried out within the scope of this invention consisted in particular in developing a method for detecting a chemical transformation. Thus, this invention proposes solving the problems reported above by using a method for measuring a chemical transformation that is reliable, sensitive and reproducible, using a stable substrate within the environment in which the chemical reaction occurs, and such that the successive transformations release a detectable product.

SUMMARY AND OBJECTS OF THE INVENTION

This invention has as its object a method for releasing at least one product that can be detected, characterized in that a compound of Formula (II') below:

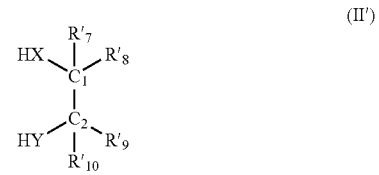

is subjected

To a chemical oxidation that cleaves the bond $C_1$-$C_2$ to obtain the product, in the compound of Formula (II'):

$R'_7$ to $R'_{10}$, which are identical or different, correspond to a hydrogen atom, a substituted or unsubstituted alkyl group, or a substituted or unsubstituted functional group, X and Y, which are identical or different, are selected from among an oxygen atom, a sulfur atom, an amine of Formula —$NR_{11}R_{12}$, and $R_{11}$ is selected from among: a hydrogen atom, an alkyl group, and s substituted or unsubstituted aryl group, and $R_{12}$ is not a hydrogen atom.

This chemical oxidation reaction is carried out with an oxidizing chemical agent that can correspond advantageously and in a non-limiting way to one or more of the following reagents: $H_5IO_6$, $RuO_2$, $OsO_4$, $(CH_3CH_2CH_2)_4N(RuO_4)$, $NaClO_4$, $NaIO_4$, $Na_3H_2IO_6$, $NaMnO_4$, $K_2OsO_4$, $KIO_4$, $KMnO_4$, $KRuO_4$, $K_2RuO_4$, LiOCl, lead acetate, tetrapropylammonium periodate, chromic acid or salts of the latter, NaBiO3, Ph3BiCO3, $Ca(OCl)_2$, the reagents Ce(IV), Cr(VI), the salts of Co (II), IOAc, I(OAc)3, N-iodosuccinimide, VO(OAc), $Pb(OAc)_4$, $MnO_2$, $H_2O_2$ or the mixture of the reagents [$H_2O_2$, $Na_2WO_4$, $H_3PO_4$].

Quite preferably the oxidizing chemical agent is a periodate salt.

Said product, released directly or indirectly, can be a volatile molecule or an active substance that can modulate a function such as in particular a pharmacological substance or else a detectable compound.

DETAILED DESCRIPTION OF PREFERRED EMBODIMENTS

Within the meaning of this invention there fall the following definitions:

Volatile molecule: one or more molecules by themselves or in combination that have the property of being volatile, in particular any aldehyde-type or volatile ketone-type molecule, such as, for example, numerous perfumes or numerous bioactive molecules such as the pheromones.

Active substance: one or more molecules by themselves or in combination that can modulate a function such as in particular a pharmaceutical substance that can modulate, for example, a hormonal action, a physiological action (blood pressure, mood, waking state), or a malignant development (tumor). The active substances can also correspond to molecules that have properties that can cure or prevent a pathology. The active substances can also have an antibiotic or insecticide effect or exhibit specific properties of odor or taste.

Specific compound: one or more compounds that can exhibit by themselves or in combination a variation of their biophysical, biological or chemical properties before and after the chemical oxidation stage, such as in particular a spectral-type variation or a variation of the solubility.

Chemical oxidation: any chemical reaction that is carried out in the presence of a chemical reagent that can oxidize the product of Formula (II') and that induces a cleavage of the bond between carbons C1 and C2.

Functional group: any chemical group that belongs to a class of organic compounds that is characterized by chemical properties. By way of example of a functional group, it is possible to cite: amides, acyls, alkoxy, nitrites, aryls, heteroaryls, alkenyls, carbonyls, thiocarbonyls, carboxyls, thiocarboxyls, carbamyls, thiocarbamyls, thiocarbamides, alcohols, thiols, or amines that may or may not be substituted.

Direct release: the release of product that is obtained immediately after said chemical oxidation reaction.

Indirect release: the release of the product that is obtained after one or more secondary reactions, in particular a chemical reaction, after said chemical oxidation reaction. The secondary reaction can correspond, by way of example, to a beta-elimination reaction. Indirect releases are also those that result from the exposure of a product that is obtained immediately after said chemical oxidation reaction to irradiation or to the action of enzymes that are more or less specific. These secondary reactions can allow in particular the monitoring of the release of said product.

In the case of a direct release, the released product corresponds to the Formula $R'_7R'8C_1=X$ and/or $R'_9R'_{10}C_2=Y$, in which R'7 to R'10, X, and Y have the same meanings as above.

In the case of an indirect release, the released product corresponds to the product of at least one secondary reaction that is carried out on at least one compound of Formula $R'_7R'_8C_1=X$ or $R'_9R'10C_2=Y$, in which $R'_7$ to $R'_{10}$, X, and Y have the same meanings as above.

The product that is released in a direct or indirect manner can be detected; mention is then made of detectable product that corresponds to a detectable volatile molecule, to a detectable active substance or else to a detectable specific compound.

In the case of the direct or indirect release of a volatile molecule, an active substance or a specific compound, the compound of Formula (II') makes it possible to release, after the chemical oxidation, respectively at least one volatile molecule, at least one active substance or at least one specific compound.

It is known that, for example, the pinacol groups or the vicinal diol groups, just like the amino-alcohol groups, are not sensitive to the oxidation of air and are not volatile. They can therefore be used as stable derivatives of the volatile molecule, which will be released in particular in a controlled manner by exposure of said derivatives to an oxidizing agent, such as periodate.

Thus, in the case where the released product corresponds to a volatile molecule, the method of the invention can be used to implement an atomizer of a volatile molecule, and said volatile molecule will be released gradually from a substrate by a chemical oxidation of the latter.

In the case where the product corresponds to an active substance, the method of the invention can be used to release a galenical form of a medication.

The invention therefore also has as its object a composition that comprises a compound of Formula (II') from which it is possible to release a product directly or indirectly by the method of the invention.

Such a composition can be useful, by way of example, for the preparation of an atomizer of a volatile molecule, comprising a mixture of at least one compound of Formula (II') and an oxidizing agent such as periodate.

According to a preferred implementation, the composition of the invention comprises an inert solid matrix or a galenical form of a medication.

By way of example, the volatile molecule can be a perfume or a bioactive molecule such as a pheromone. Respectively a perfume atomizer or a mosquito-repellant sprayer is then considered.

More particularly, the volatile molecule is selected from among the group that comprises: benzaldehyde (artificial almond), butanal, citronellal, anisaldehyde, menthone, cuminaldehyde, salicylaldehyde (used in perfumery), vanillin, phenylacetaldehyde (hyacinth) or isovaleraldehyde (lemon, mint, eucalyptus).

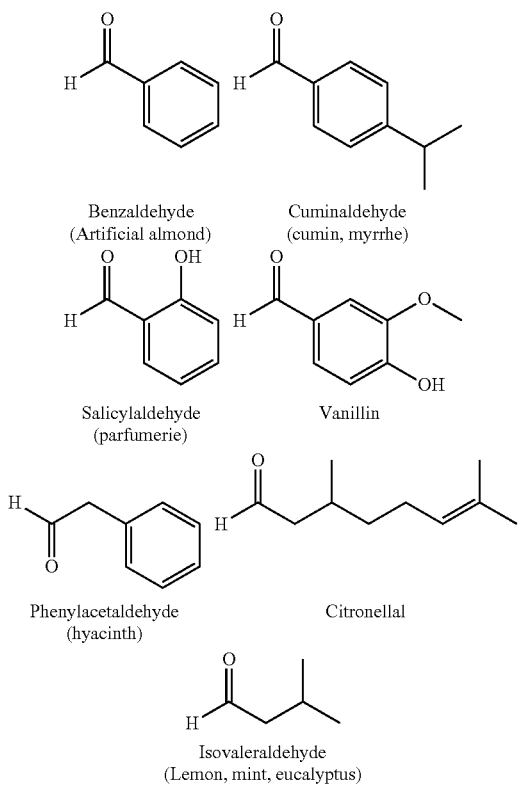

Benzaldehyde
(Artificial almond)

Cuminaldehyde
(cumin, myrrhe)

Salicylaldehyde
(parfumerie)

Vanillin

Phenylacetaldehyde
(hyacinth)

Citronellal

Isovaleraldehyde
(Lemon, mint, eucalyptus)

Advantageously, the active substance as defined in the invention is selected from among the group that comprises: testosterone, estrone or nicotine.

The method for releasing the product according to the invention can also comprise a preliminary stage for preparing the compound of Formula (II') by any technique that is known to one skilled in the art.

It is, for example, the preparation of a stable derivative of a volatile molecule or an active substance or a specific compound.

It can be, for example, the preparation of a vicinal diol or an amino alcohol of said product by any technique that is known to one skilled in the art.

According to a particular implementation, the invention has as its object a method for releasing at least one product that comprises the following stages:

a) the preparation of a compound of Formula (II')

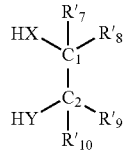

(II')

in which the bond $C_1$-$C_2$ is sensitive to a cleavage by a chemical oxidation reaction, and $R'_7$, $R'_8$, $R'_9$, $R'_{10}$, X and Y have the same meaning as above, b) the chemical oxidation of the compound of Formula (II') that is obtained at stage (a) that cleaves the bond $C_1$-$C_2$ to obtain said product.

Preparation stage (a) can comprise at least one chemical transformation and/or at least one enzymatic transformation.

The preparation of the compound of Formula (II') can be done, for example, by obtaining the reduced form of the ketone or aldehyde function of at least one of said products of Formula $R'_9R'_{10}C_2$=Y and/or $R'_7R'_8C_1$=X.

Thus, stage (a) can be, for example, a reaction for dimerization of at least one volatile molecule, in particular an aldehyde or a ketone.

Advantageously, the reaction for dimerization of stage (a) of the method for releasing a product of the invention can be carried out by biosynthesis of vicinal diols.

Such reactions for dimerization of a product to obtain a stable derivative are, for example, those described in FIG. 7, attached, in which:

a first dimerization reaction according to stage (a) is a reducing dimerization of aldehyde 1 or ketone 2 of the released product in the presence of zinc, so as to obtain a pinacol group.

A second dimerization reaction according to stage (a) is carried out in two stages, by olefination of carbonyl in the presence of a phosphorated ylide, followed by a dihydroxylation by osmium tetroxide. This second approach leads to a terminal diol that, after oxidation by the sodium periodate, releases 1 equivalent of formaldehyde.

By way of examples of synthesis of a compound of Formula (II'), in the case of volatile molecules, it is possible to cite:

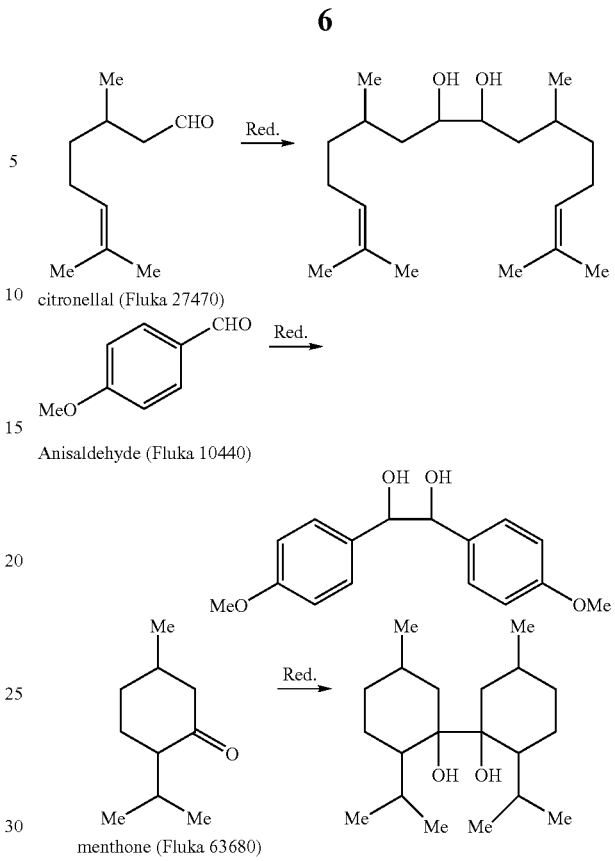

citronellal (Fluka 27470)

Anisaldehyde (Fluka 10440)

menthone (Fluka 63680)

Particular implementations of the method for releasing a volatile molecule carried out by the applicant within the scope of this invention are provided in detail in the examples below in which diols are used:

1—A symmetric diol, hydrobenzoin, obtained by reduction by sodium borohydride from benzoin, makes it possible to obtain benzaldehyde, with the odor of almond, by chemical oxidation.

2—The oxidation of 1,2-pentanediol is also illustrated; it releases an aliphatic aldehyde, butanal, that has an odor of butter.

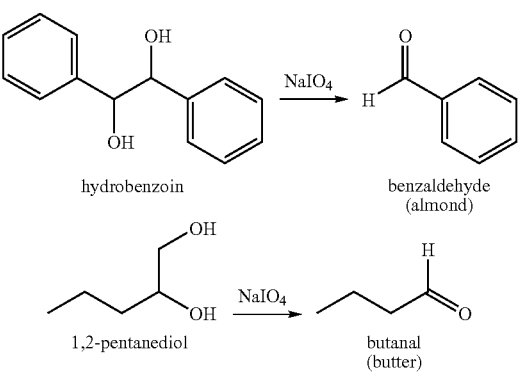

hydrobenzoin → benzaldehyde (almond)

1,2-pentanediol → butanal (butter)

Particular implementations of the method for releasing an active substance within the scope of this invention are provided in detail in the examples below.

The first two examples correspond to direct releases of the active substance and the last example to an indirect release in which the oxidation reaction is followed by a beta elimination.

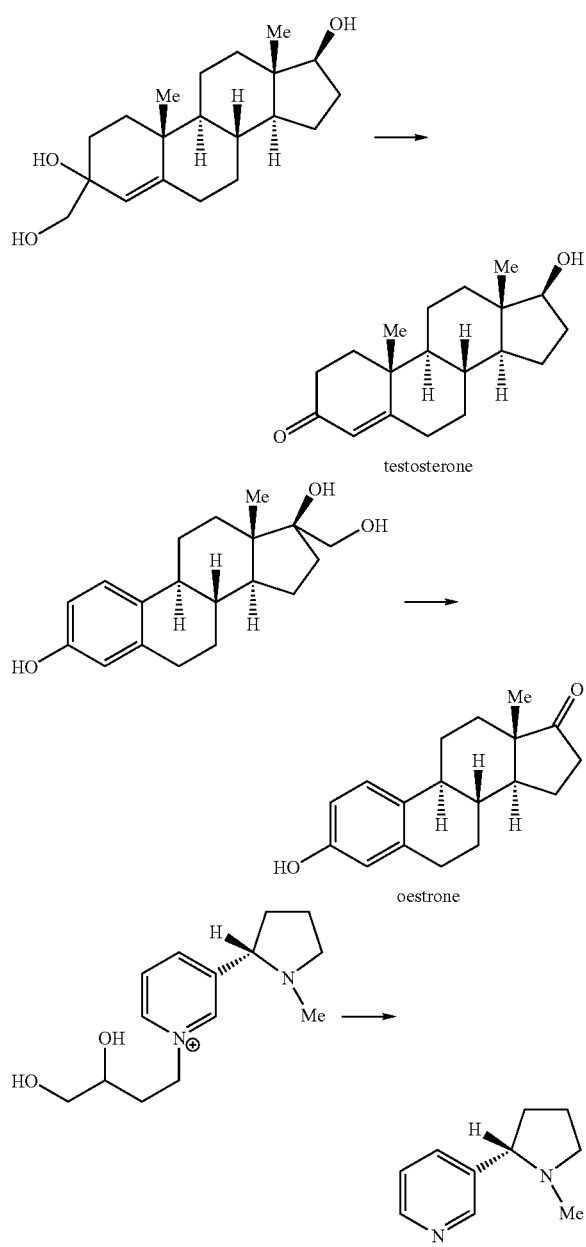

testosterone oestrone

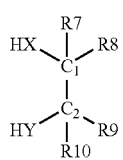

nicotine

The method of the invention is noteworthy in that the released product is a detectable product; it can then be used to detect a chemical transformation.

Advantageously, when the method of the invention has as its object the release of a detectable product, the compound of Formula (II') is a compound of Formula (II)

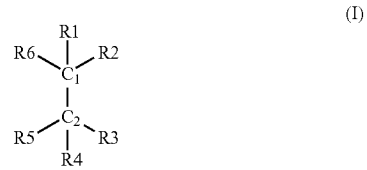

(II)

in which,

X and Y, which are identical or different, are selected from among an oxygen atom, a sulfur atom, an amine of Formula $-NR_{11}R_{12}$, and $R_{11}$ is selected from among: a hydrogen atom, an alkyl group, an aryl group that may or may not be substituted, and $R_{12}$ is not a hydrogen atom, $R_7$ to $R_{10}$, which are identical or different, are selected from among a hydrogen atom, an alkyl group that may or may not be substituted, or a functional group that may or may not be substituted, and at least one of groups $R_7$ to $R_{10}$ is a group Di, which is insensitive to the stage (b) chemical oxidation reaction and which exhibits detectable properties, directly or indirectly, alone or in combination, after the cleavage of the bond $C_1$-$C_2$.

These properties are characteristic of the detectable product.

By way of example, these properties can be biophysical, biological or chemical, such as in particular a spectral-type variation or a solubility variation.

The compound of Formula (II) corresponds to a particular implementation of the compound of Formula (II'), thus the statements made regarding the compound of Formula (II') are valid for the compound of Formula (II).

The detectable product can then be released after having carried out a first chemical transformation stage of a substrate to obtain a compound of Formula (II) then a second chemical oxidation stage of said compound of Formula (II).

The detection of this transformation is obtained by using the method for releasing a detectable product or by carrying out a chemical transformation of a substrate that produces the compound of Formula (II), then by chemically oxidizing the compound of Formula (II) to release the product that can be detected. In this case, the release of the detectable product comprises the following stages:

a) the chemical transformation of a substrate of Formula (I) in which the bond C1-C2 is insensitive to a cleavage by a chemical oxidation reaction:

(I)

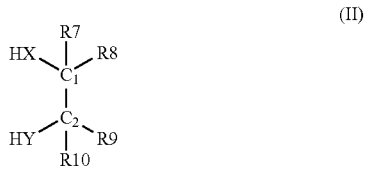

into a compound of Formula (II) in which the bond $C_1$-$C_2$ is sensitive to a cleavage by a chemical oxidation reaction:

(II)

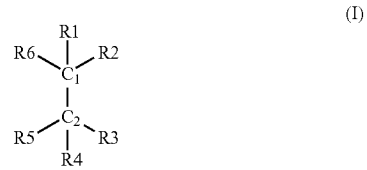

and b) the chemical oxidation of the compound of Formula (II), obtained in stage (a), that cleaves the bond $C_1$-$C_2$ to obtain a detectable product directly or indirectly, and in that in the compounds of Formulas (I) and (II):

At least one of groups $R_1$ to $R_6$ is a group Di as defined above,

Groups $R_1$ to $R_6$, which are identical or different, are selected from among: a hydrogen atom, an alkyl group that may or may not be substituted, a functional group that may or may not be substituted, and in the case of a functional group of Formulas $OR_{12}$, $-SR_{12}$, and $-NR_{11}R_{12}$, $R_{11}$ is selected from among: a hydrogen atom, an alkyl group, an aryl group that may or may not be substituted, and $R_{12}$ is not a hydrogen atom, Group or groups $R_1$ to $R_6$ that form after stage (a) the groups of Formulas —XH and —YH are insensitive to stage (b) oxidation or can be sensitive to this oxidation if the corresponding compound of Formula (I) does not produce the compound of Formula (II) during an oxidation of the type of that of stage (b), X and Y, which are identical or different, are selected from among an oxygen atom, a sulfur atom, or an amine of Formula —$NR_{11}R_{12}$, $R_7$ to $R_{10}$, which are identical or different, are either identical to at most four of the groups $R_1$ to $R_6$, or, because of the transformation of one or more of groups $R_1$ to $R_6$, during the reaction of stage (a), selected from among a hydrogen atom, an alkyl group that may or may not be substituted, or a functional group that may or may not be substituted, and at least one of groups $R_7$ to $R_{10}$ is a group Di as defined above.

After stage (b), the method of the invention obviously comprises a stage for direct or indirect detection of the detectable product to carry out, for example, the detection of the chemical transformation of stage (a).

The method of the invention accepts several preferred meanings of groups $R_1$ to $R_6$, among which the following cases are considered more particularly:

$R_1$ to $R_6$ are selected so that the bond $C_1$-$C_2$ is part of at least one cycle, At least one pair of groups $R_1$ to $R_6$ together form an oxygen atom, a sulfur atom, or a group of Formula —$NR_{11}R_{12}$, At most one pair of groups $R_1$ to $R_6$, one of which is selected from among $R_1$, $R_2$, and $R_6$, and the other is selected from among $R_3$, $R_4$ and $R_5$ form a double bond between carbons $C_1$ and $C_2$, At most two pairs of groups $R_1$ to $R_6$, one of which is selected from among $R_1$, $R_2$ and $R_6$, and the other is selected from among $R_3$, $R_4$ and $R_5$, form a triple bond.

A diagram example for detecting a chemical transformation of a substrate according to the invention is shown in FIG. 1, attached, whereby the compounds of Formulas (III) and (IV) are directly or indirectly detectable.

An advantageous implementation of the method for releasing a detectable product comprises the following stages:

(a) the transformation of a substrate of Formula (I') in which the bond $C_1$-$C_2$ is insensitive to a cleavage by a chemical oxidation reaction:

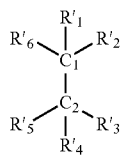
(I')

into a compound of Formula (II') in which the bond $C_1$-$C_2$ is sensitive to a cleavage by a chemical oxidation reaction

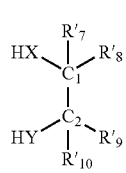
(II')

and (b) the chemical oxidation of the compound of Formula (II') that is obtained in stage (a) in the presence of a compound of Formula II that cleaves the bond $C_1$-$C_2$ to obtain directly or indirectly at least one detectable product, where, in the compound of Formula (I'):

Groups $R'_1$ to $R'_6$, which are identical or different, are selected from among: a hydrogen atom, an alkyl group that may or may not be substituted, a functional group that may or may not be substituted, and in the case of a functional group of Formulas —$OR_{12}$, —$SR_{12}$, and —$NR_{11}R_{12}$, $R_{11}$ is selected from among: a hydrogen atom, an alkyl group, an aryl group, that may or may not be substituted, and $R_{12}$ is not a hydrogen atom, Group or groups $R'_1$ to $R'_6$ that form after stage (a) the groups of Formulas —XH and —YH are insensitive to stage (b) oxidation or can be sensitive to this oxidation if the corresponding compound of Formula (I') does not produce the compound of Formula (II') during an oxidation of the type of that of stage (b), in the compound of Formula (II'):

X and Y, which are identical or different, are selected from among an oxygen atom, a sulfur atom, an amine of Formula —$NR_{11}R_{12}$, and $R_{11}$ is selected from among: a hydrogen atom, an alkyl group, an aryl group, that may or may not be substituted, and $R_{12}$ is not a hydrogen atom, $R'_7$ to $R'_{10}$, which are identical or different, are either identical to at most four of groups $R'_1$ to $R'_6$, or, because of the transformation of one or more of groups $R_1$ to $R_6$, during the reaction of stage (a), selected from among a hydrogen atom, an alkyl group that may or may not be substituted, or a functional group that may or may not be substituted, and in the compound of Formula (II):

$R_7$ to $R_{10}$, which are identical or different, correspond to a hydrogen atom, an alkyl group that may or may not be substituted, a functional group that may or may not be substituted, and at least one of groups $R_7$ to $R_{10}$ is a group Di as defined above, X and Y, which are identical or different, are selected from among an oxygen atom, a sulfur atom, an amine of Formula —$NR_{11}R_{12}$, and $R_{11}$ is selected from among: a hydrogen atom, an alkyl group, an aryl group, that may or may not be substituted, and $R_{12}$ is not a hydrogen atom.

This advantageous implementation puts the compound of Formula (II'), obtained from the chemical transformation of the compound of Formula (I'), into competition with the compound of Formula (II) during oxidation stage (b). The oxidation speed of the compound of Formula (II) will therefore decrease proportionately to the amount of compound of Formula II' that is formed. The signal that is associated with the transformation of the compound of Formula (II), detectable thanks to the presence of a group Di that is a precursor of a detectable product, will therefore also decrease proportionately to the amount of compound of Formula (II') that is produced.

In this manner, it is possible to detect via the compound of Formula (II) the chemical reaction that transforms the compound of Formula (I') into a compound of Formula (II').

In this advantageous implementation, the substrate of Formula (I') can correspond to the non-modified specific substrate of the chemical transformation such as, for example, the non-modified specific substrate of an enzyme.

The method of the invention also accepts a modification of one of groups $R_7$ to $R_{10}$ except for Di, by the chemical oxidizing agent of stage (b), provided that this disturbs the cleavage of the bond $C_1$-$C_2$ neither during stage (b) nor during the subsequent detection.

In a particular implementation of the process of the invention where stages (a) and (b) are simultaneous, group or groups $R_1$ to $R_6$ are insensitive to stage (b) oxidation.

Under these conditions, the reaction of chemical transformation and chemical oxidation take place under the same experimental conditions. When stages (a) and (b) are carried out simultaneously, the profile of the signal that is obtained can give information about the kinetic course of the transformation if the latter is limiting in the process, i.e., slower than the oxidation.

In another implementation, stages (a) and (b) are not simultaneous. Groups $R_1$ to $R_6$ then may or may not be sensitive to the oxidation of stage (b). Transformation reaction (a) can take place under experimental conditions that may or may not be similar to the oxidation reaction (b). When stages (a) and (b) are not simultaneous, a reaction speed that is proportional to the amount of accumulated product will be obtained.

The method of the invention can be used with a substrate that comprises several chemical groups that can be transformed in stage (a) and several chemical groups that are precursors of detectable products.

According to the chemical transformation that is being studied and/or the structure of the substrate that is used, the method of the invention can be carried out in a suitable reaction medium that is selected from among an aqueous, organic, two-phase or solid medium.

In this case,
chemical transformation or chemical reaction means any transformation of a substrate that may or may not be spontaneous and that can call for particular experimental conditions such as heat, UV, etc. In the case of a non-spontaneous chemical transformation, the reaction can call for a chemical reagent or a catalyst such as an enzyme. This chemical transformation of stage (a) can be carried out with several sequential reactions that may or may not be simultaneous.

Groups $R_1$ to $R_{10}$, regardless of their meaning, can consist of or comprise an isotope, such as, for example, deuterium. In addition, advantageously, groups $R_1$ to $R_{10}$ are stable in a reaction medium, in particular an aqueous, organic, two-phase, or solid medium, etc.

Advantageously, the substrate that is used in the process of the invention comprises one or more chiral centers. The substrate that is used in the process of the invention can therefore consist of a mixture of enantiomers, or diastereomers or enantiomers that are pure.

Preferred substrates that correspond to Formula I are described below.

A first class of substrate (I) corresponds to Formulas (V) to (IX) below:

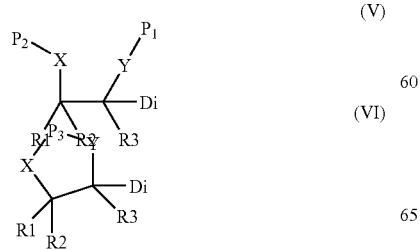

(V)

(VI)

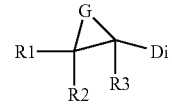

(VII)

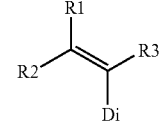

(VIII)

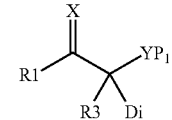

(IX)

in which:
Di is a group as defined above
$R_1$ to $R_3$ and X and Y have the same meanings as above,
At most one of groups $P_1$ and $P_2$ is a hydrogen atom. $P_1$ and $P_2$, which are identical or different, are selected from among an acyl group that is substituted by an aryl or alkyl or peptidyl group, a phosphate group, a phosphate ester group, a phosphonate group, a carbamyl group that is substituted by an aryl or acyl or peptidyl group, a glycosyl group and a sulfate group,
$P_3$ is selected from among a carbonyl group, a group —$PO_2R_{11}$ or a group $R_{11}PO$—, where $R_{11}$ has the same meaning as above, a group —$SO_2$, a group —$CHOR_{13}$ where $R_{13}$ represents an aryl, alkyl or glycosyl group, a group $SiR_{14}R_{15}$ where $R_{14}$ and $R_{15}$, which are identical or different, represent an aryl, alkyl, aryloxy or alkoxy group, and a group $AsO_2H$—,
G is selected from among an oxygen atom, a sulfur atom, or an amine group of Formula $NR_{11}R_{12}$ where $R_{11}$ has the same meaning as above.

The product of the substrate that is obtained after the first stage of the method of the invention from substrates of Formulas (V), (VI), (VII), (VIII) and (IX) corresponds to Formula (II) or advantageously to Formula (X) below:

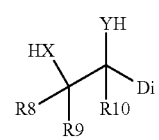

(X)

in which Di, X, Y, $R_8$, $R_9$ and $R_{10}$ have the same meaning as above.

In a particular case, the production of the substrate that is obtained after first chemical transformation stage (a) of the invention from substrates of Formulas (I) can also correspond to Formula (XV) below:

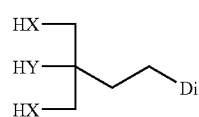

(XV)

in which X, Y and Di have the same meaning as above, whereby the chain that carries Di can be in 1-, 2- or 3-position of the glycerol-containing derivative.

Entirely preferably, groups X and Y of the compound of Formula (XV) are hydroxyl groups.

The detection of the chemical transformation according to the invention is used either by a direct revelation or by an indirect revelation of the compound that is obtained after the chemical oxidation of the compound of Formulas (II) or (X) carried out with an oxidizing chemical agent according to stage (b).

Tetrapropyl ammonium periodate, soluble in organic phase, is advantageously used when the method of the invention is carried out in an organic medium.

According to a type of preferred revelation named direct revelation below, according to which the compound that corresponds to Formula (XI) obtained after the chemical oxidation reaction that is carried out on the derivative that corresponds to Formulas (II) or (X) after stage (b) is directly detectable according to the diagram below.

Direct Revelation

An embodiment of the invention with a direct revealing uses the direct detection of a property of the compound of Formula (XI), not present in the compounds of Formulas (I) or (II) or (X).

In a type of direct revelation or direct releasing of a detectable product:

Di in the compound of Formula (X) is a precursor of a detectable product, and

Di in the compound of Formula (XI) has directly detectable properties.

By way of non-limiting examples, it is possible to cite among these properties of compound (XI): a physical property, such as solubility; a physicochemical property, such as a spectral property; or a biological property, such as the activation of an enzyme, an odor, or the action of a pheromone.

The molecule that corresponds to Formula (XI) can correspond to aromatic ketones, for example a beta-aromatic ketone that is detected by a spectral variation, an aldehyde such as benzaldehyde or citronellal that is detected by odor, or to a pheromone that is detected by the attraction of insects. (Suzuki et al., (1980). Agric. Biol. Chem. 44, 2519 and Millar et al. (1996). Bioorg. Med. Chem. 3, 331-340).

In a second type of preferred revelation, named indirect revelation below, compound (XII), obtained after chemical oxidation stage (b) of the compound of Formulas (II) or (X), undergoes a beta-elimination reaction that produces detectable product ZH, according to the diagram below.

Indirect Revelation beta-elimination

The group Di that corresponds to Formula (XIII) below:

(XIII)

in which:

$R_{16}$, $R_{17}$ and $R_{18}$, which are identical or different, represent a hydrogen atom, an alkyl group that may or may not be substituted or a functional group that may or may not be substituted, and Z is a precursor of detectable product ZH.

In this type of indirect revelation or indirect release of a detectable product:

Di in the compounds of Formulas (X) and (XII) is the precursor of said detectable product that will be released after a secondary beta-elimination reaction.

In this embodiment of the invention with an indirect revelation, the detection of a property of product ZH that is obtained by a beta-elimination reaction that is carried out on the compound of Formula (XII) that is obtained after chemical oxidation stage (b) is carried out. This beta-elimination reaction, advantageously spontaneous, is preferably carried out in the presence of a base called B that can correspond to bovine serum albumin (BSA).

Among the properties of compound ZH, it is possible to cite as non-limiting examples a physical property such as solubility; a physicochemical property such as a spectral property; or a biological property such as the induction of bacterial growth.

Compound ZH is selected from among an aromatic alcohol, a heteroaromatic alcohol, a heteroaromatic amine, a halogen atom, or a phosphoric ester. By way of non-limiting examples, there can be cited: fluorescein, phenolphthalein, phenol red, p-nitrophenol, o-nitrophenol, 2,4-dinitrophenol, 6-hydroxynaphthoic acid, 8-hydroxy-pyrene 1,3,6-trisulfonic acid, tyrosine, luciferin, indolyl, 5-bromo-4-chloro-indolyl, quinolinium, nitro-anilinium or pyridoxamine.

In a third type of preferred revelation, the compound that is obtained after stage (a) for chemical transformation of the substrate corresponds to Formula XIV below:

(XIV)

in which:

Di, R8, R9, X and Y have the same meanings as above, and,

The two groups Di, which are identical or different, one attached to carbon $C_1$, the second attached to carbon $C_2$, interact with one another.

In this case, the cleavage of the bond $C_1$-$C_2$ to this compound (XIV) causes a detectable spectral variation.

A non-limiting example of interaction between the two groups Di is a FRET-type energy transfer.

A diagram that shows this revelation using a FRET-type energy transfer is shown in FIG. 2, attached.

Examples of substrates that allow the implementation of the invention with a direct revelation are compounds of Formula (V) in which groups X, Y, $R_1$, $R_2$, $R_3$ and Di are selected from among those that are described in the following table.

For all of the compounds that are described in the following tables that illustrate particular examples of substrates according to the invention, the stereochemistry is always carried out in all of the possible variants.

TABLE I

| No. | X  | Y | $R_1$      | $R_2$ | $R_3$ | Di                   |
|-----|----|---|------------|-------|-------|----------------------|
| 6   | NH | O | H          | H     | H     | 6'-Methoxy-2'-naphthyl |
| 7   | NH | O | COOH       | H     | H     | 6'-Methoxy-2'-naphthyl |
| 8   | NH | O | CONH—peptide | H   | H     | 6'-Methoxy-2'-naphthyl |
| 17  | O  | O | H          | H     | H     | 6'-Methoxy-2'-naphthyl |

The group 6'-methoxy-2'-naphthyl corresponds to the formula:

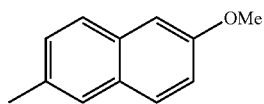

Examples of substrates that allow the implementation of the invention with an indirect detection are compounds of Formula (V) in which groups X, Y, $R_{11}$, $R_{12}$, $R_{13}$ as well as groups $R_1$, $R_2$, $R_3$ and ZH are selected from among those that are described in Table II below.

TABLE II

| No. | X  | Y  | $R_1$     | $R_2$  | $R_3$ | $R_{16}$     | $R_{17}$ | $R_{18}$ | Z          |
|-----|----|----|-----------|--------|-------|--------------|----------|----------|------------|
| 1   | NH | O  | H         | H      | H     | H            | H        | H        | Coum*/NP** |
| 2   | NH | O  | $CH_2$    | H      | H     | H            | $CH_2$   | H        | Coum*/NP** |
| 3   | NH | O  | COOH      | H      | H     | H            | H        | H        | Coum*/NP** |
| 4   | NH | O  | CONH-peptide | H   | H     | H            | H        | H        | Coum*/NP** |
| 5   | NH | O  | H         | H      | Me    | H            | H        | H        | Coum*/NP** |
| 9   | O  | O  | H         | H      | H     | H            | H        | H        | Coum*/NP** |
| 10  | O  | O  | Me        | Me     | H     | H            | H        | H        | Coum*/NP** |
| 11  | O  | O  | H         | $CH_2$ | H     | H            | $CH_2$   | H        | Coum*/NP** |
| 12  | O  | O  | (MeO)CHO  | H      | H     | O—CH(OMe)    | H        | H        | Coum*/NP** |
| 13  | O  | O  | H         | H      | Me    | H            | H        | H        | Coum*/NP** |
| 14  | O  | O  | Et        | H      | H     | H            | H        | H        | Coum*/NP** |
| 15  | O  | O  | (MeO)CHO  | H      | H     | O—CH(OMe)    | H        | H        | Coum*/NP** |
| 16  | O  | O  | (Ade)CHO  | H      | H     | O—CH(Ade)    | H        | H        | Coum*/NP** |
| 18  | NH | NH | H         | H      | H     | H            | H        | H        | Coum*/NP** |

*Coum = 7-oxycoumarin

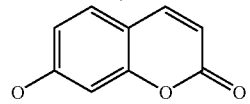 [SMILES: O=c1ccc2ccc(O)cc2o1]

**NP = paranitro-phenoxy

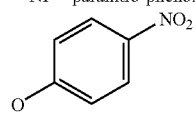

The structures that correspond to substrates of Table II are shown below:

Amino alcohols

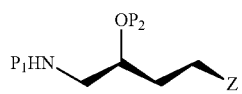

(1)

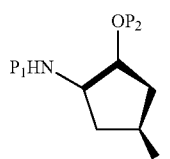

(2)

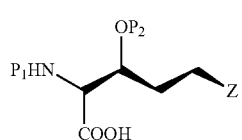

(3)

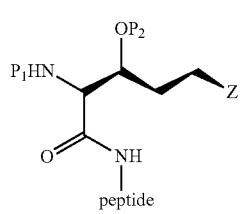

(4)

-continued

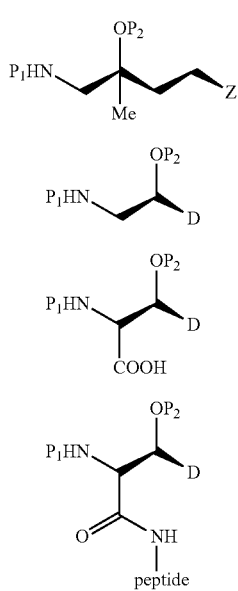

(5)

(6)

(7)

(8)

Diamines

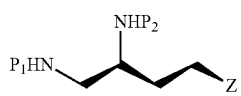

(18)

The diamines can be mono- or disubstituted, whereby groups $P_1$ and $P_2$ cannot both correspond to H.

$P_1$ and/or $P_2$ can correspond to:

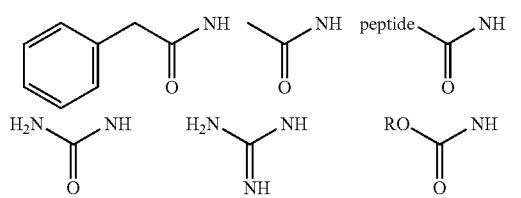

R = Bn, Me, Et, t-Bu

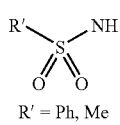

R' = Ph, Me

Diols:

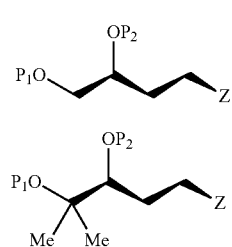

-continued

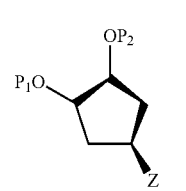

(11)

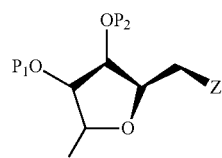

(12)

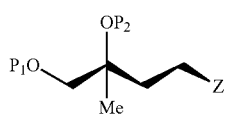

(13)

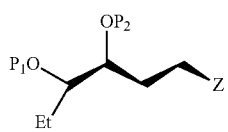

(14)

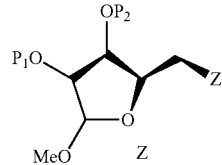

(15)

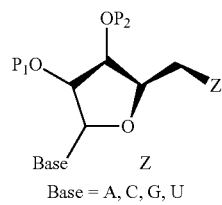

(16)

Base = A, C, G, U

The diols can be mono- or disubstituted.

In the particular case of a disubstitution, the two hydroxyl radicals can be substituted identically as follows:

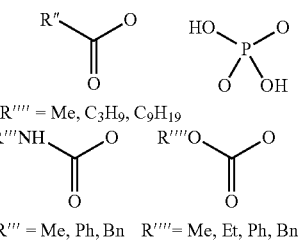

R'''' = Me, C$_3$H$_9$, C$_9$H$_{19}$

R''' = Me, Ph, Bn   R'''' = Me, Et, Ph, Bn

In the case of a mono-substitution, by way of a particular example, the hydroxyl radicals can be monofunctionalized as above, and in addition as follows:

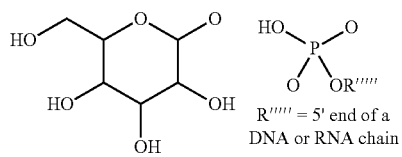
R''''' = 5' end of a DNA or RNA chain

By way of a particular implementation example of the invention, the revelation of stage (b) is carried out sequentially by using substrates that are at least disubstituted such as the disubstituted substrate of Formula XVII below:

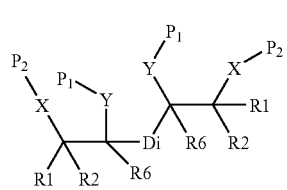
(XVII)

in which: Di, $R_1$, $R_2$, $R_6$, $P_1$, $P_2$, X and Y have the same meanings as above.

A preferred embodiment of the method of the invention that uses a substrate that corresponds to Formula (V) above comprises the transformation of mono- or diester derivatives of diols (1 a/b) by a lipase or an esterase to produce compound (2) according to the diagram below.

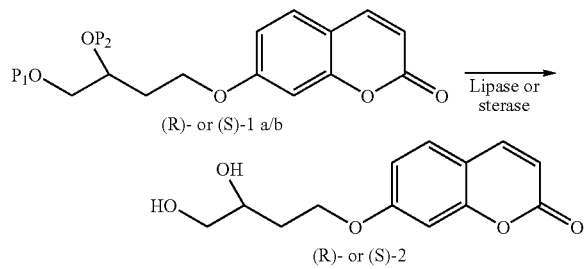

Another preferred embodiment of the method of the invention that uses a substrate that belongs to the second class above comprises the transformation of mono- or diester derivatives of diols (3 a/b) by a lipase or an esterase to produce compound (4) according to the diagram below.

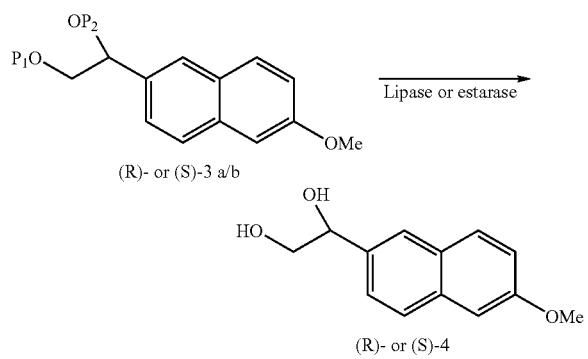

By way of example of substrates of Formula (VI), it is possible to cite more particularly those that correspond to the formulas below:

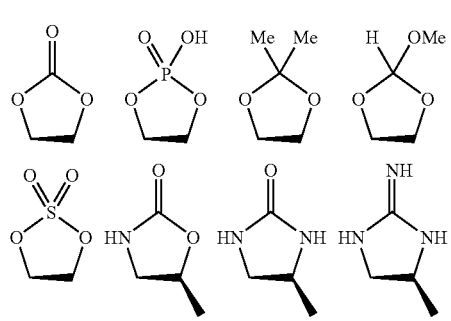

By way of example of substrates of Formula (VII) that is used in the method of the invention with a direct revelation, it is possible to cite more particularly those that are described in Table III below:

TABLE III

| No. | $R_1$ | $R_2$ | $R_3$ | $R_{16}$ | $R_{17}$ | $R_{18}$ | Z |
|---|---|---|---|---|---|---|---|
| 19 | H | H | H | H | H | H | coum/NP |
| 20 | H | H | Me | H | H | H | coum/NP |
| 21 | Me | Me | H | H | H | H | coum/NP |
| 22 | Et | H | H | H | H | H | coum/NP |
| 23 | CH$_2$— | H | H | H | CH$_2$— | H | coum/NP |

Coum and NP have the same meanings as above.

By way of example of substrates of Formula (VII) that is used in the method of the invention with an indirect revelation, it is possible to cite more particularly those that are described in Table IV below:

TABLE IV

| No. | $R_1$ | $R_2$ | $R_3$ | Di |
|---|---|---|---|---|
| 24 | H | H | H | naphth |

The structures that correspond to the substrates of Tables III and IV are shown below:

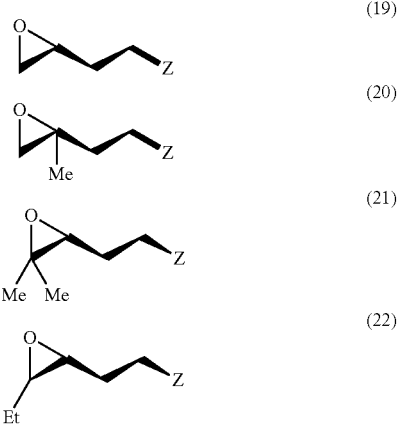

(23)

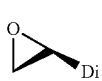
(24)

A preferred embodiment of the method of the invention that uses a substrate that corresponds to Formula (VII) above comprises the transformation of epoxide (7) by an epoxide esterase to produce compound (2) according to the diagram below.

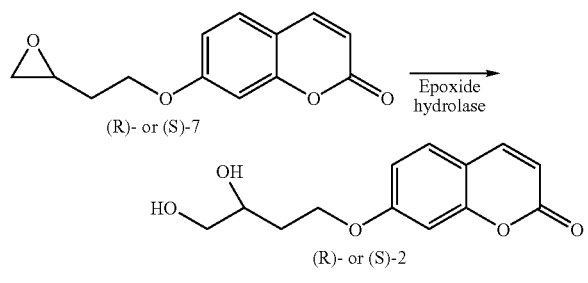

Another preferred embodiment of the method of the invention that uses a substrate that corresponds to Formula (VII) above comprises the transformation of epoxide (8) by an epoxide hydrolase to produce compound (4) according to the diagram below.

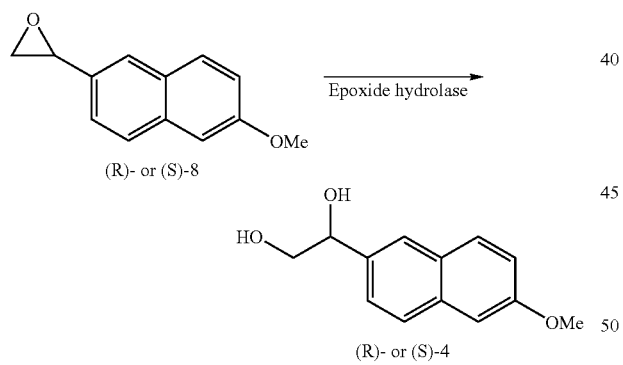

By way of example of substrates of Formula (VIII) that is used in the method of the invention with an indirect revelation, it is possible to cite more particularly those that are described in Table V below, where the groups coum and NP have the same meanings as above.

TABLE V

| No. | $R_1$ | $R_2$ | $R_3$ | $R_{16}$ | $R_{17}$ | $R_{18}$ | Z |
|---|---|---|---|---|---|---|---|
| 25 | H | H | H | H | H | H | coum/NP |
| 26 | H | H | Me | H | H | H | coum/NP |
| 27 | Me | Me | H | H | H | H | coum/NP |

TABLE V-continued

| | | | | | Di | | |
|---|---|---|---|---|---|---|---|
| No. | $R_1$ | $R_2$ | $R_3$ | $R_{16}$ | $R_{17}$ | $R_{18}$ | Z |
| 28 | Et | H | H | H | H | H | coum/NP |
| 29 | CH$_2$— | H | H | H | CH$_2$— | H | coum/NP |

By way of example of substrates of Formula (VIII) that are used in the method of the invention with a direct revelation, it is possible to cite more particularly those that are described in Table VI below:

TABLE VI

| No. | $R_1$ | $R_2$ | $R_3$ | Di |
|---|---|---|---|---|
| 30 | H | H | H | naphth |

The structures that correspond to the substrates of Tables V and VI are shown below:

(25)

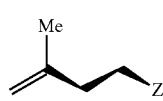
(26)

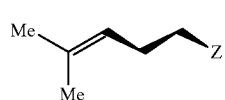
(27)

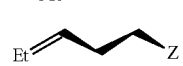
(28)

(29)

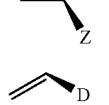
(30)

A preferred embodiment of stage (a) of the method of the invention that uses a substrate according to Formula (VIII) above comprises the transformation of olefin (9) by a dihydroxylase or a chemical catalyst such as an alkaloid or an amino alcohol in the presence of OsO4 to produce compound (2) according to the diagram below:

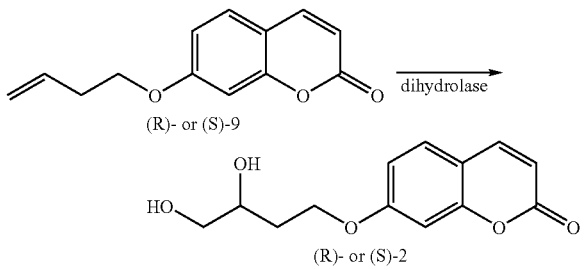

Another preferred embodiment of stage (a) of the method of the invention that uses a substrate according to Formula (VIII) above comprises the transformation of olefin (10) by a dihydroxylase to produce compound (4) according to the diagram below.

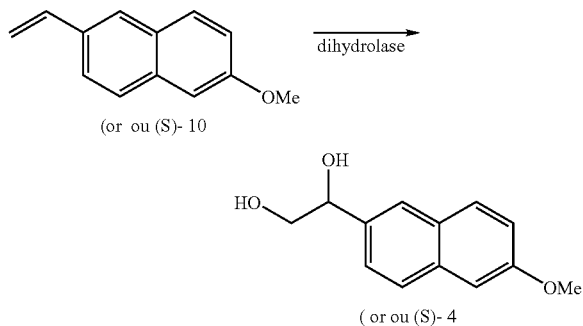

(or ou (S)- 10)

(or ou (S)- 4)

By way of example of oxidation reaction, according to stage (b), products that are obtained from stage (a), it is possible to cite the two reactions below:

With a direct revelation method

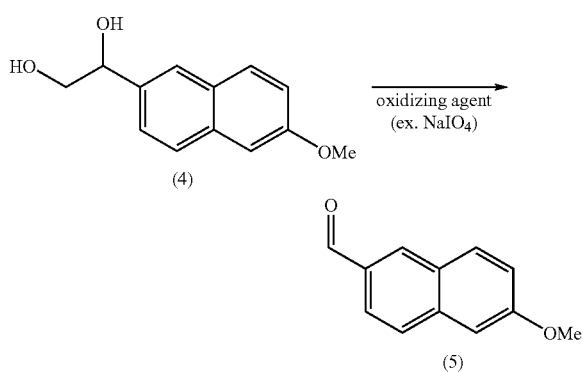

(4)

(5)

With an indirect revelation method

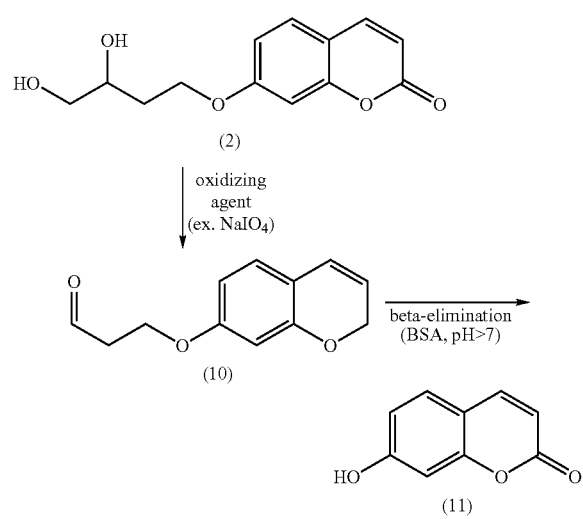

(2)

(10)

(11)

The invention also relates to the substrates that correspond to Formulas (V), (VI), (VII), (VII) or (IX).

These substrates have a particular advantage, and in particular, they are able to be used in the method that is described above.

Advantageously, these substrates are stable in the reaction medium, in particular in the very wide ranges of pH and temperature, but also in very diverse solvents.

By way of example, substrates that can be used in the method of the invention are shown in Table XI, attached.

The invention also has as its object a composition that comprises at least one compound of Formula (II').

This compound of Formula (II') can correspond to a form that is stabilized by a volatile molecule, an active substance or a specific compound.

Advantageously, the composition according to the invention comprises an oxidizing agent.

The method of the invention is noteworthy in that it makes it possible to detect a chemical transformation that is optionally present in a sample by selecting a substrate that is the most suitable for the transformation that it is desired to analyze.

Advantageously, these substrates have various degrees of specificity. These degrees of specificity are provided by the structure of one or more groups $R_1$ to $R_6$ of Formula (I) or $R_1$ to $R_3$, or G, or $P_1$ to $P_3$ of Formulas (V), (VI), (VII), (VIII) or (IX).

By way of example, in the case of the detection of a chemical transformation that is carried out by a lipase, group or groups $R_1$ to $R_6$ are selected so that the substrates that correspond to Formula (I) are close to the structure of the specific substrate. In particular, they can correspond to a fatty acid chain. One skilled in the art will know, based on the type of chemical transformation to be detected, to adapt the selection of group or groups $R_1$ to $R_6$. In the case of implementing the method of the invention, where two compounds of Formula (II) are put into competition at stage (2), the substrate of Formula (I) can correspond to the non-modified specific substrate of the enzyme, which represents an advantage in the case of use of the method of the invention for the identification of new catalysts or of the new activity of known catalysts that can transform a substrate of Formula (I) or (I') respectively into a compound of Formula (II) or (II').

The method of the invention makes it possible to identify an enantioselective or stereoselective chemical transformation in a sample.

Advantageously, the chemical transformation is carried out with a catalyst and in particular an enzyme. By way of non-limiting example, the method of the invention makes possible the detection of the activity of an enzyme that is selected from among: lipase, esterase, protease, glycosidase, glycosyl transferase, phosphatase, kinase, mono- or dioxygenase, haloperoxidase, lignin peroxidase, diarylpropane peroxidase, epoxide hydrolase, nitrile hydratase, nitrilase, transaminase, amidase, acylase, dihydroxylase, phytase, xylanase, nuclease, and reductase.

In the case of a chemical transformation that may or may not be spontaneous, it is possible to cite in particular: a spontaneous or thermal hydrolysis of an ester, an olefin dihydroxylation by AD-mix reagents, and a hydrolysis of epoxides by chromium complexes.

The invention therefore finally relates to a process for detecting and/or quantifying a known chemical transformation in a sample that consists of using the method for detecting a chemical transformation described above in the presence of said sample and a substrate that is suitable for the desired activity.

The invention also makes it possible to detect the substrate of Formula (I) or (I') in the presence of a chemical or biochemical catalyst reagent.

The method of the invention can be used for screening, particularly at a high flow rate, a catalyst from an in vivo or in vitro expression library. These libraries can be prepared, for example, from microorganisms or microalgae that preferably have extremophile properties.

The method of the invention can also be used to identify catalysts that have a different activity relative to a starting activity. These catalysts will be, for example, products of directed mutagenesis or directed evolution.

A particular embodiment of the method of the invention relates to the case where the substrate of Formula (I) or (I') is itself the product of a first unknown chemical transformation, whose activity is desired to be identified.

By way of example of this particular embodiment of the process of the invention, it is possible to cite the epoxidation reaction of olefins to transform them into epoxides of Formulas (I) or (I') or (VII), and said epoxides then undergo an enzymatic reaction to obtain the diols of Formulas (II) or (II') or (X), which will be subjected to a chemical oxidation reaction by the periodate.

The method of the invention is noteworthy in that it also makes possible the identification and the isolation of new chemical or biochemical catalysts that can transform a substrate of Formula (I) or (I') respectively into a compound of Formula (II) or (II'). Actually, the method of the invention makes it possible to disclose the presence of a catalyst that, thanks to chemical oxidation, generates a signal that is directly or indirectly detectable.

Consequently, the invention also has as its object the use of the method for detecting a chemical transformation, as described above, for the identification of new catalysts, or the new activity of a known catalyst. The invention also relates to a catalyst that can be identified by the method of the invention.

These new catalysts are specific to the experimental conditions used during their detection; they advantageously correspond to enzymes.

These new enzymes are specific to the experimental conditions that are used during their detection.

Other advantages and characteristics of the invention will emerge from reading the examples below that are part of the experimental works carried out by the applicant within the scope of the invention and where reference is made to the accompanying figures in which:

FIG. 3 represents the enzymatic activity of the *Candida antarctica* lipase based on the temperature. The enzymatic reactions were carried out in the PIPES buffer (0.1 M, pH 7) at 50, 60, 70, 80 and 95° C. for 40 minutes by using 2-hydroxy-4-p-nitrophenyl-butyl-decanoate. (■) *Candida antarctica* lipase; (□) without enzyme.

I—Synthesis of the Substrates

Example 1

Preparation of 4-(7-coumarinyloxy)-1-butene

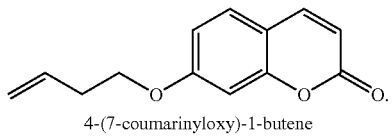 [SMILES: C=CCCOc1ccc2ccc(=O)oc2c1]

4-(7-coumarinyloxy)-1-butene

Figure 1:
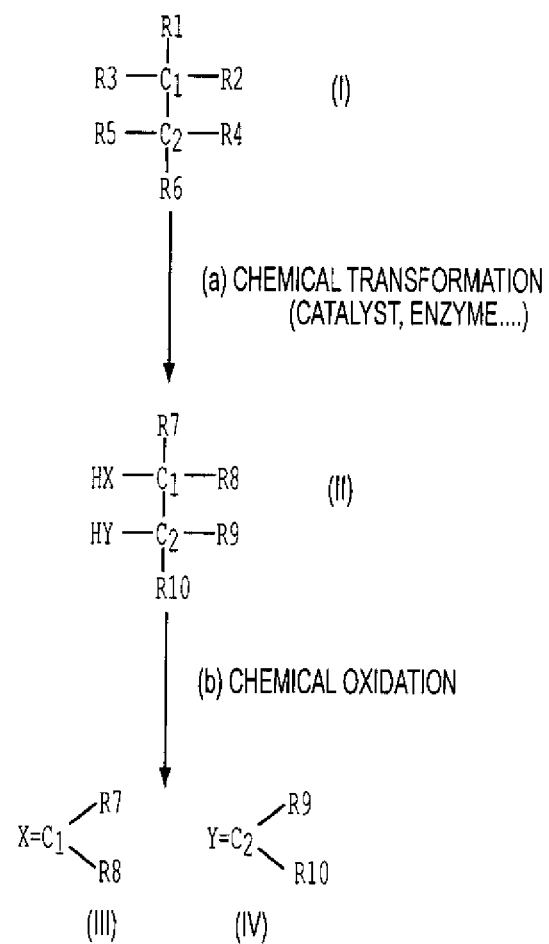
Figure 2:
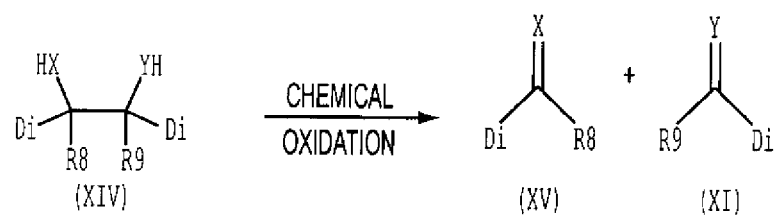
Figure 3:
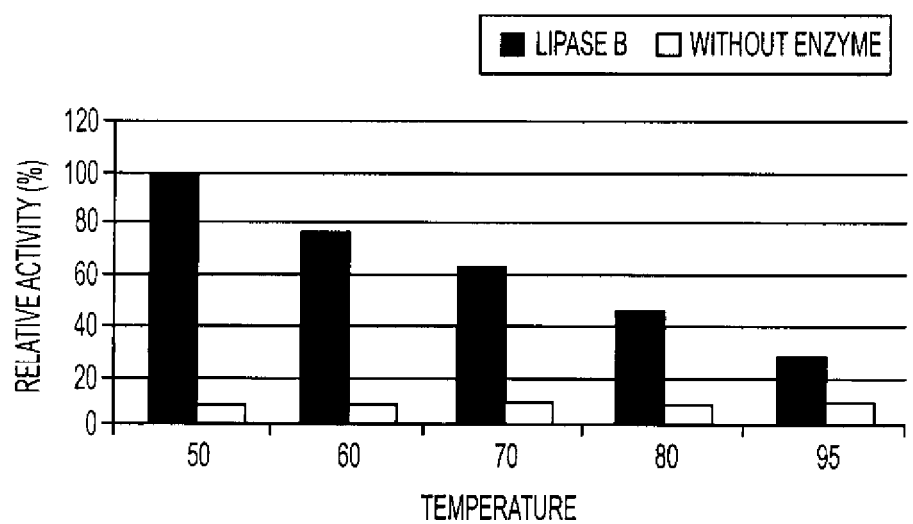
Figure 4:
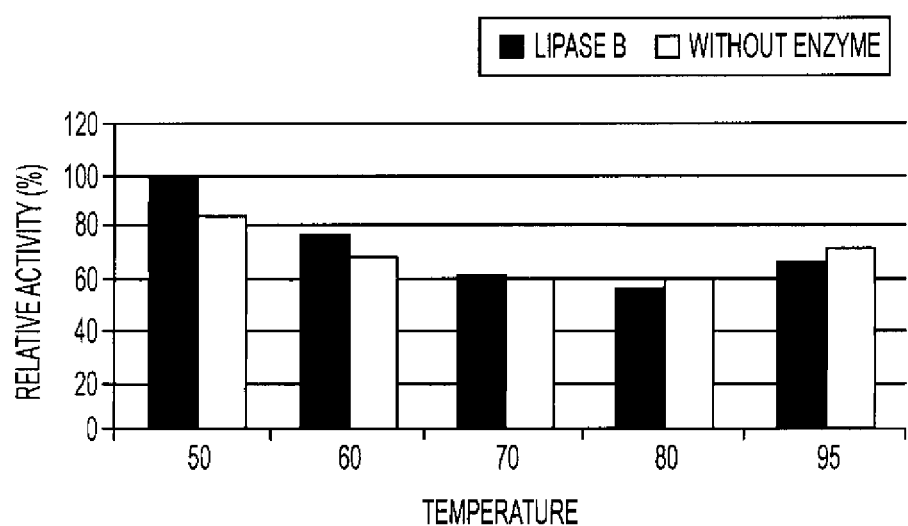
FIG. 4 illustrates the enzymatic activity of the *Candida antarctica* lipase based on the temperature. The enzymatic reactions were carried out in the PIPES buffer (0.1 M, pH 7) at 50, 60, 70, 80 and 95° C. for 40 minutes by using para-nitrophenylbutyrate. (■) *Candida antarctica* lipase; (□) without enzyme.
Figure 5:
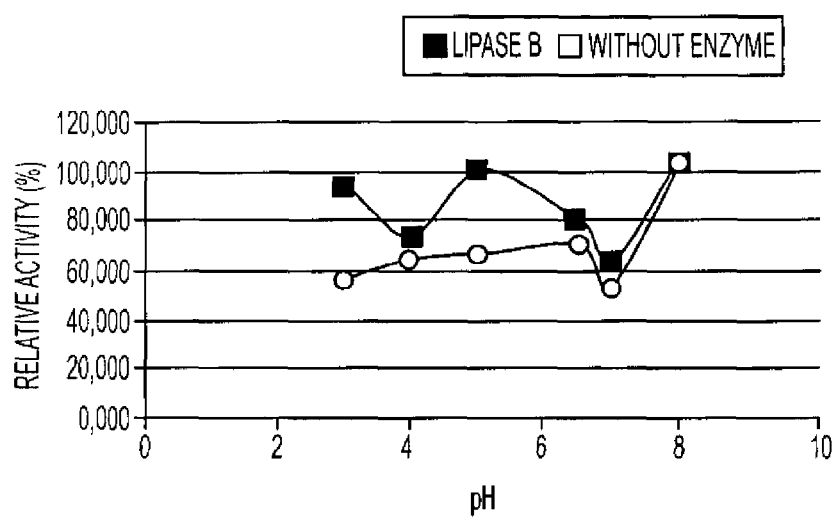
FIG. 5 illustrates the activity of the *Candida antarctica* lipase based on the pH of the solution. The tests were carried out by using 2-hydroxy-4-p-nitrophenyl-butyl-decanoate.
Figure 6:
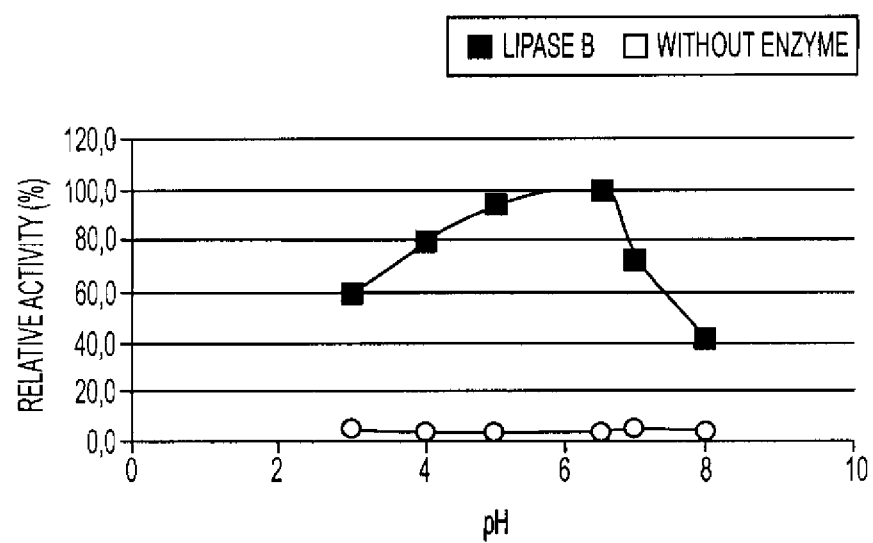
FIG. 6 illustrates the activity of the *Candida antarctica* lipase based on the pH of the solution. The tests were carried out by using para-nitrophenolbutyrate.
Figure 7:
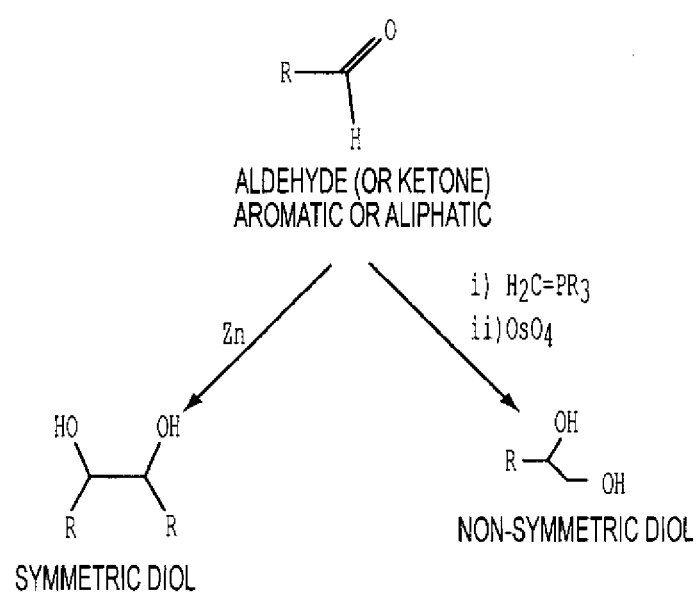

A suspension of 7-hydroxycoumarin (3 g, 19.6 mmol) in DMF (20 ml) is treated with NaH (60% suspension in oil, 1.03 g, 25.9 mmol), then with 4-bromo-1-butene (2.65 g, 19.6 mmol). It is heated to 60° C. for 24 hours, then it is diluted with ethyl acetate (400 ml), and it is washed with water (3×300 mL) then with 1 M NaOH (3×200 ml). The residue is chromatographed with the mixture (ethyl acetate-hexane) to obtain 4-(7-coumarinyloxy)-1-butene (2.7 g, 67%).

Example 2

Preparation of (S)-4-(7-coumarinyloxy)-1,2-butanediol

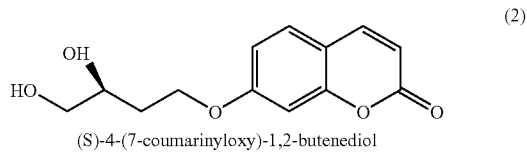 [SMILES: O=c1ccc2ccc(OCC[C@H](O)CO)cc2o1]

(S)-4-(7-coumarinyloxy)-1,2-butenediol

An AD-alpha-mix suspension (4.2 g) is stirred in 30 ml of t-BuOH/water 1:1 until a single phase is obtained (5 minutes). It is then cooled to 0° C., and olefin is added (0.648 g, 3 mmol). After 16 hours at 0° C., it is quenched with $Na_2S_2O_5$ (4.5 g). After one hour at ambient temperature, it is extracted with $CH_2Cl_2$ and chromatographed ($CH_2Cl_2$/acetone elution 7:3) to obtain 0.6 g (80%) of pure diol (S).

Melting point 92-93° C., $[a]_D^{20}$=−22.4 (c 0.46, $CH_3OH$); $^1$H-NMR ($CD_3OD$) 7.83 (d, 1H, J=9.8 Hz), 7.47 (d, 1H, J=8.3 Hz), 6.85-6.92 (m, 2H), 6.21 (d, 1H, J=9.3 Hz), 4.16-4.23 (m, 2H), 3.81-3.93 (m, 1H), 3.54 (d, 2H, J=6.35 Hz), 1.97-2.13 (m, 1H), 1.74-1.91 (m, 1H).

The same procedure with the AD-beta-mix provides enantiomer R.

Example 3

Preparation of (S)-4-(7-coumarinyloxy)-1,2-epoxybutane

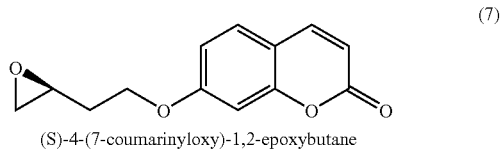 [SMILES: O=c1ccc2ccc(OCC[C@H]3CO3)cc2o1]

(S)-4-(7-coumarinyloxy)-1,2-epoxybutane

Trimethyl orthoacetate (1 ml), then pyridinium paratoluene sulfonate (1 mg) are added to a solution of (S)-4-(7- coumarinyloxy)-1,2-butanediol (0.15 g, 0.6 mmol) in CH$_2$Cl$_2$. After 40 minutes, it is evaporated in its entirety, the residue is dissolved in CH$_2$Cl$_2$ (1 ml), and it is treated with Me$_3$SiCl (0.1 ml, 0.78 mmol). After one hour, dry methanol (1 ml) and potassium carbonate (0.2 g, 1.5 mmol) are added. It is left for 2 hours at 20° C., then it is filtered, and the filtrate (hexane/ethyl acetate 6:4) is chromatographed to obtain the epoxide (S) (0.097 g, yield 70%).

Melting point 61-64° C., $[\alpha]_D^{20}$=−23.0 (c 0.3, CHCl$_3$); $^1$H-NMR (CDCl$_3$): 7.58 (d, 1H, J=9.3 Hz), 7.31 (d, 1H, J=8.3 Hz), 6.75-6.81 (m, 2H), 6.18 (d, 1H, J=9.8 Hz), 4.03-4.19 (m, 2H), 3.05-3.14 (m, 1H), 2.78 (t, 1H, J=4.9 Hz), 2.53 (dd, 1H, J=4.9 and 2.4 Hz), 2.04-2.20 (m, 1H), 1.79-1.97 (m, 1H).

The same procedure with (R)-4-(7-coumarinyloxy)-1,2-butanediol provides enantiomer R.

Example 4

Preparation of
(S)-1,2-Diacetoxy-4-(7-coumarinyloxy)-butane

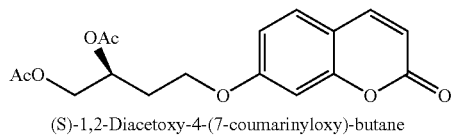 [SMILES: CC(=O)OC[C@H](CCOc1ccc2ccc(=O)oc2c1)OC(C)=O]

(S)-1,2-Diacetoxy-4-(7-coumarinyloxy)-butane 2 ml of acetic anhydride is added to a solution of (S)-4-(7-coumarinyloxy)-1,2-butanediol (0.1 g, 0.4 mmol) in 4 ml of anhydrous pyridine at 0° C. After 18 hours at 20° C., it evaporated with toluene, and the residue is chromatographed to obtain diacetate S (quantitative yield).

Melting point 74-76° C., $[\alpha]_D^{20}$=−9.8 (c 0.5, CHCl$_3$); $^1$H-NMR (CDCl$_3$): 7.61 (d, 1H, J=9.8 Hz), 7.34 (d, 1H, J=8.8 Hz), 6.74-6.82 (m, 2H), 6.22 (d, 1H, J=9.3 Hz), 5.24-5.35 (m, 1H), 4.32 (dd, 1H, J=11.7 and 3.4 Hz), 3.97-4.15 (m, 2H), 4.10 (dd, 1H, J=11.7 and 5.9 Hz), 2.05-2.16 (m, 2H), 2.05 (s, 6H).

The same procedure with (R)-4-(7-coumarinyloxy)-1,2-butanediol provides enantiomer R.

Example 5

Preparation of (S)-1-Acetoxy-4-(7-coumarinyloxy)-2-butanol

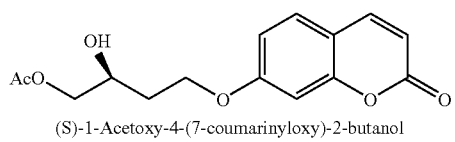 [SMILES: CC(=O)OC[C@@H](O)CCOc1ccc2ccc(=O)oc2c1]

(S)-1-Acetoxy-4-(7-coumarinyloxy)-2-butanol

Acetyl chloride (0.36 mmol, 0.024 ml) is added to a solution of (S)-4-(7-coumarinyloxy)-1,2-butanediol (0.090 g, 0.36 mmol) and triethylamine (0.1 ml, 0.72 mmol) in 8 ml of dry CH$_2$Cl$_2$. After 40 minutes at 0° C., it is diluted with CH$_2$Cl$_2$, and it is washed with an aqueous solution of NaHCO$_3$. The chromatography of the residue after evaporation provides monoacetate S (0.058 g, 0.22 mmol, 60%).

$[\alpha]_D^{20}$=−9.6 (c 0.31, CHCl$_3$); $^1$H-NMR (CDCl$_3$): 7.61 (d, 1H, J=9.8 Hz), 7.33 (d, 1H, J=7.8 Hz), 6.78-6.83 (m, 2H), 6.21 (d, 1H, J=8.8 Hz), 4.01-4.29 (m, 5H), 2.09 (s, 3H), 1.91-2.00 (m, 2H).

The same procedure with (R)-4-(7-coumarinyloxy)-1,2-butanediol provides enantiomer R.

Example 6

Preparation of
1-Amino-4-(7-coumarinyloxy)-2-butanol

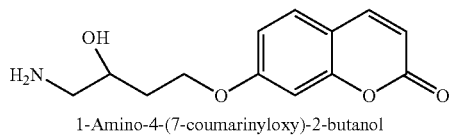 [SMILES: NCC(O)CCOc1ccc2ccc(=O)oc2c1]

1-Amino-4-(7-coumarinyloxy)-2-butanol 5 ml of 30% aqueous ammonia and Gd (OTf$_3$) (0.039 g, 0.065 mmol) are added to a solution of racemic 4-(7-coumarinyloxy)-1,2-epoxybutane (0.150 g, 0.65 mmol) in 2 ml of ethanol. It is heated at 65° C. for 15 hours, the solvent is evaporated, the residue is diluted in ethyl acetate, and it is washed with an NaCl-saturated solution. The residue provides the crude amine (0.081 g, yield 50%) that is used without purification for the next stage.

Example 7

Preparation of
1-Phenylacetamido-4-(7-coumarinyloxy)-2-butanol (5)

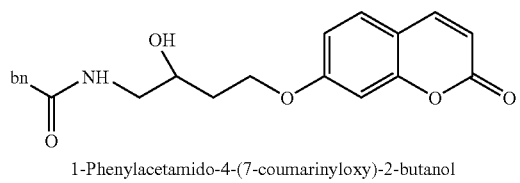

1-Phenylacetamido-4-(7-coumarinyloxy)-2-butanol

Triethylamine (1.3 mmol, 0.18 ml), then phenotype chloride (0.65 mmol, 0.085 ml) are added to a solution of 1-amino-4-(7-coumarinyloxy)-2-butanol (0.162 g, 0.65 mmol) in 3 ml of dry CH$_2$Cl$_2$ at 0° C. It is stirred at 0° C. for 2 hours, then it is diluted with CH$_2$Cl$_2$ and washed with an NaHCO$_3$-saturated aqueous solution. The crude product is chromatographed to obtain the amide (0.170 g, 0.48 mmol, 74%).

Example 8

Preparation of 6-Methoxy-2-naphthaldehyde and 6-dimethylamino-2-naphthaldehyde

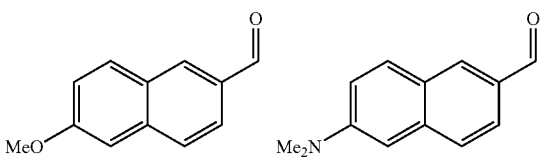 [SMILES: COc1ccc2cc(C=O)ccc2c1 ; CN(C)c1ccc2cc(C=O)ccc2c1]

6-Methoxy-2-naphthaldehyde and
6-dimethylamino-2-naphthaldehyde

6-Methoxy-2-naphthaldehyde is prepared by successive treatment of 2-bromo-6-methoxynaphthalene in solution in dry ether with n-butyllithium and then dimethylformamide. (Literature: *J. Med. Chem.* 1998, 1308-1312). 6-Dimethylamino-2-naphthaldehyde is prepared according to the described procedure (Barbas et al., *Proc. Natl. Acad. Sci. USA* 1998, 95, 15351) as follows: gaseous dimethylamine is introduced into a mixture of 2.4 ml of dry benzene and 2.4 ml of hexamethylphosphoramide (HMPA) until 750 mg (16.7 mmol) is dissolved. At 0° C. and under inert atmosphere, n-butyllithium (1.6 M in hexane, 16.7 mmol) is added, then after 15 minutes, 6-methoxy-naphthaldehyde (390 mg, 2.09 mmol) is added. Stirring is continued for 14 hours at 20° C., then it is poured into aqueous phosphate buffer, pH 7.4, and it is extracted with ether. Purification by chromatography provides 6-dimethylamino-2-naphthaldehyde (350 mg, 84%).

6-Methoxy-2-naphthaldehyde: $^1$H-NMR (CDCl$_3$): 10.09 (s,1H), 8.26 (s,1H), 7.78-7.95 (m, 3H), 7.17-7.26 (m, 2H), 3.96 (s, 3H).

Example 9

Preparation of 6-Methoxy and 6-Dimethylamino-2-vinylnaphthalene

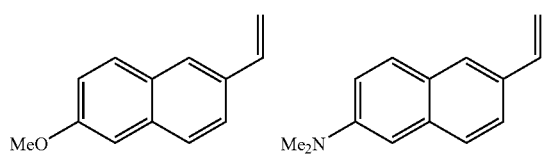

6-Methoxy and 6-dimethylamino-2-vinylnaphthalene

6-Methoxy-naphthaldehyde (432 mg, 2.35 mmol) is added to a solution of instantaneous ylide (Ph$_3$P$^+$Br$^-$+NaNH$_2$, 1.48 g, 2.4 mmol) in anhydrous THF (5 ml). After one hour of stirring at ambient temperature, it is diluted with ether, it is filtered on Celite, and it is chromatographed (hexane/AcOEt 5:1) to obtain 6-methoxy-2-vinyl-naphthalene (390 mg, 90%).

6-Methoxy-2-vinyl-naphthaldehyde: $^1$H-NMR (CDCl$_3$): 7.59-7.74 (m, 4H), 7.11-7.16 (m, 2H), 6.86 (dd, 1H, J=17.3 and 10.9 Hz), 5.82 (d, 1H, J=17.6 Hz), 5.28 (d, 1H, J=10.7 Hz), 3.93 (s, 3H).

Example 10

Preparation of (R) and (S) 6-Methoxy-2-(1',2'-dihydroxyethyl)naphthalene

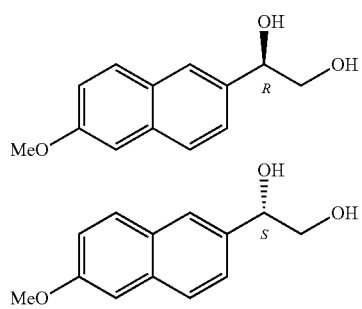

(R) and (S) 6-Methoxy-2-(1',2'-dihydroxyethyl)naphthalene

These products, in the form of enantiomers R (>99% ee) and S (>99% ee), were prepared by Shamisens asymmetric dihydroxylation of the corresponding olefin as described above for coumarin derivatives.

Diol: $^1$H-NMR (Acetone-d6): 7.71-7.84 (m, 3H), 7.52 (dd, 1H, J=8.5 and 1.5 Hz), 7.25-7.31 (m, 1H), 7.16 (dd, 1H, J=8.9 and 2.5), 4.87 (dd, 1H, J=7.5 and 4.2 Hz), 3.94 (s, 3H), 3.50-3.80 (m, 4H, CH$_2$O+2 OH).

Example 11

Preparation of (R)- and (S)-2-(6-Methoxy-2-naphthyl)oxyran

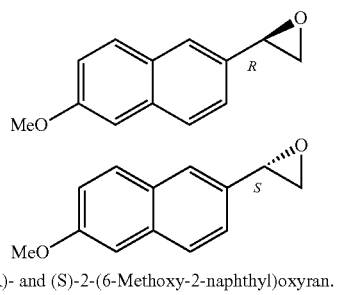

(R)- and (S)-2-(6-Methoxy-2-naphthyl)oxyran.

These products were prepared from corresponding diols according to the method that is described above for the coumarin derivatives and obtained optically pure (ee>99% according to chiral HPLC).

$^1$H NMR (CDCl3): 7.70-7.75 (m, 3H), 7.26-7.32 (m, 1H), 7.13-7.19 (m, 2H), 4.00 (dd, 1H, J=4.1 and 2.4 Hz), 3.92 (s, 3H), 3.22 (dd, 1H, J=5.4 and 4.0 Hz), 2.91 (dd, 1H, J=5.4 and 2.4 Hz).

II—Oxidation by Periodate

The oxidation of 1,2 diols and amino alcohols by periodate in an aqueous medium is a reaction that is well known to one skilled in the art. This reaction provides a purely chemical alternative for the conversion of alcohols into carbonyl groups in aqueous medium with a high chemoselectivity in the presence of other functional groups. The applicant now found that, advantageously, hydrolytic enzymes that release diols or amino alcohols from substrates that are resistant to oxidation by periodate can be detected by fluorescence in the presence of periodate and bovine serum albumin (BSA).

Diesters (R)—(S) as well as monoesters (R)— and (S)— represented by Formula (I) (compounds 1 a/b, 3 a/b) constitute excellent substrates for lipases and esterases given their structural similarity with glycerides. The amides that are shown by Formula I (compound 5) react with the amidases and peptidases. Epoxides (R)— and (S)— that are represented by Formula (II) (compounds 7 and 8) react with the epoxy-hydrolase enzymes. The applicant thus found that the transformation undergone by these fluorogenic substrates transformed by sodium periodate, in the presence of hydrolytic enzymes, provides a new method for detecting said enzymes.

III—Stability of the Substrates

The substrates acetates 1, amide 5 and epoxide 6 are stable in the presence of periodate and BSA without the aqueous media. Under the same conditions, diol 2 and amino alcohol 6 release umbelliferone. Under optimized reaction conditions using 100 μm of substrate, 1 mmol of sodium periodate, 2 mg/ml of BSA in a borate buffer with a pH of 8.8, diol 2 is transformed into umbelliferone with a yield of 72% without observable secondary reactions. The oxidation yield is independent of the presence of BSA, which indicates that these reagents do not interfere with one another in a notorious manner. The oxidation of amino alcohol 6 takes place with a yield of 85% under the same conditions.

IV—Development of the Test

Acetates 1, amide 5 and epoxides (R)-7 and (S)-7 were tested in the presence of corresponding hydrolytic enzymes. The acetates were tested compared to 25 different esterases and lipases. The epoxides were tested compared to the epoxyhydrolase extracted from *Aspergillus Niger* (X-J. Chen, A. Archelas, R. Furstoss, J. Org. Chem. 1993, 58, 5528) and *Rhodotorula glutinis* (C. A. G. M. Weijers, A. L. Botes, M. S. van Dyk, J. A. M. de Bont, Tetrahedron Asymm. 1998, 9, 467).

Phenylacetamide 5 was tested against penicillin G acylase, chymotrypsin and papain. An increase of fluorescence that is clearly dependent on time is observed when the enzymatic activity is present. The analyses that are carried out by high-pressure liquid chromatography (HPLC) confirm that the increase of fluorescence is caused by the release of umbelliferone from substrates.

In all of the cases, the results that are obtained are similar at both pH 7.2 and pH 8.8.

All of the enzymes that showed activity against any substrate preserve their activity regardless of whether preincubation of the enzyme with the substrate is done before the addition of periodate and BSA or during the reaction, in the presence of all of the components. This clearly proves that the addition of periodate and BSA as secondary agents does not affect the enzymatic activity of the enzymes that should be analyzed. The analyses by HPLC of the reaction with the active enzymes in the absence of periodate and BSA show that diol 2 and amino alcohol 6 are actually released by the enzymes that were considered as active in the fluorescence test.

V—Measurement of the Lipase Activity by Using Substrates
2-Hydroxy-4-p-nitrophenyl-butyl-decanoate and
p-Nitro-phenylbutyrate The hydrolytic activity of the *Candida antarctica* lipase was tested on 2 substrates: 2-hydroxy-4-p-nitrophenyl-butyl-decanoate and p-nitro-phenylbutyrate. The lipase activity is detected after hydrolysis of ester functions of substrates that produce the release (direct or indirect) of yellow-colored para-nitrophenol that is measured by colorimetry at 414 nm. The tests were carried out at different temperatures and pH.

The stock solutions of 2-hydroxy-4-p-nitrophenyl-butyl-decanoate and para-nitrophenolbutyrate (SIGMA) are prepared at the concentration of 20 mmol respectively in acetonitrile and isopropanol. The concentration of lipase B that is used is 0.01 mg/ml in a phosphate buffer (100 mmol, pH 7).

V.1—Measurement of the Lipase Activity Based on Temperature

V.1.1—Measurement of Lipase Activity with
2-Hydroxy-4-p-nitrophenyl-butyl-decanoate 74 μl of PIPES buffer (100 mmol, pH 7) and 10 μl of a lipase solution at 0.01 mg/ml are added to 13.6 μmol of 2-hydroxy-4-p-nitrophenyl-butyl-decanoate. The reaction is incubated in a water bath for 40 minutes at 50, 60, 70, 80 and 95° C. The samples are then removed from the water bath. Then, 40 μl of, NaIO$_4$ (100 mmol) and 4 μl of BSA (50 mg/ml) are added to the mixture. The pH of the solution is then adjusted to 10 by adding 40 μl of an Na$_2$CO$_3$ solution at 0.2 M. The para-nitrophenol that is released is then measured with a colorimeter at 414 nm.

A negative control without enzyme was carried out under the same experimental conditions.

V.1.2—Measurement of Lipase Activity with
p-Nitrophenylbutyrate

74 μl of PIPES buffer (100 mmol, pH 7) and 10 μl of a lipase solution at 0.01 mg/ml are added to 13.6 μmol of para-nitrophenylbutyrate. The reaction is incubated in a water bath for 40 minutes at 50, 60, 70, 80 and 95° C. The samples are then removed from the water bath, and the pH of the solution is adjusted to 10 with a 0.2 M Na$_2$CO$_3$ solution. The released para-nitrophenol is then measured with a colorimeter at 414 nm.

A negative control without enzyme was carried out under the same experimental conditions.

V.2.—Measurement of Lipase Activity Based on the pH of the Solution

The enzymatic activity of the *Candida antarctica* lipase was carried out at different pH levels by using buffers (100 mmol) listed in Table VII below.

TABLE VII

| Buffer | pH |
|---|---|
| Formate | 3 |
| Formate | 4 |
| Acetate | 5 |
| MES | 6.5 |
| PIPES | 7 |
| Phosphate | 8 |

V.2.1—Measurement of Lipase Activity with
2-Hydroxy-4-p-nitrophenyl-butyl-decanoate 74 μl of buffer at the desired pH (100 mmol) and 10 μl of a lipase solution at 0.01 mg/ml are added to 13.6 μmol of 2-hydroxy-4-p-nitrophenyl-butyl-decanoate. The reaction is incubated in a water bath for 40 minutes at 60° C. The samples are then removed from the water bath. Then, 40 μl of NaIO$_4$ (100 mmol) and 4 μl of BSA (50 mg/ml) are added to the mixture. The pH of the solution is then adjusted to 10 by adding 40 μl of a solution of Na$_2$CO$_3$ at 0.2 M. The para-nitrophenol that is released is then measured with a calorimeter at 414 nm.

A negative control without enzyme was carried out under the same experimental conditions.

V.2.2 Measurement of Lipase Activity with
p-Nitrophenylbutyrate

74 μl of buffer at the desired pH (100 mmol) and 10 μl of a lipase solution at 0.01 mg/ml are added to 13.6 μmol of para-nitrophenylbutyrate. The reaction is incubated in a water bath for 40 minutes at 60° C. The samples are then removed from the water bath, and the pH of the solution is adjusted to 10 with a 0.2 M Na$_2$CO$_3$ solution. The para-nitrophenol that is released is then measured with a colorimeter at 414 nm.

A negative control without enzyme was carried out under the same experimental conditions.

V.3—Results of the Detection of Lipase Activity

The 2-hydroxy-4-p-nitrophenyl-butyl-decanoate and the para-nitrophenylbutyrate commercial substrate were tested compared to the *Candida antarctica* lipase. The appearance of a yellow coloration linked to the release of para-nitrophenol is observed when hydrolytic activity is present.

The activity of the lipase based on the incubation temperature was measured by using 2-hydroxy-4-p-nitrophenyl-butyl-decanoate and the para-nitrophenylbutyrate commercial substrate. Table VIII shows the measurements of the activity of the *Candida antarctica* lipase that are made by using 2-hydroxy-4-p-nitrophenyl-butyl-decanoate and para-nitrophenylbutyrate. The activities are expressed in %. The enzymatic reactions were carried out in the PIPES buffer (0.1 M, pH 7) at 50, 60, 70, 80 and 95° C. for 40 minutes. A negative control without enzyme was also carried out by using the same experimental conditions.

TABLE VIII

| Temperature (° C.) | 2-Hydroxy-4-p-nitrophenyl-butyl-decanoate | | p-Nitrophenylbutyrate | |
| --- | --- | --- | --- | --- |
| | Lipase B | Without enzyme | Lipase B | Without enzyme |
| 50 | 100 | 8.7 | 100 | 83.6 |
| 60 | 75.9 | 9.4 | 75.4 | 67.3 |
| 70 | 61.5 | 9.5 | 60.4 | 59.5 |
| 80 | 44.2 | 8.1 | 55.9 | 59.8 |
| 95 | 26.1 | 8.6 | 66.7 | 71.5 |

The hydrolytic activity of the lipase based on the pH of the solution was also measured. Table IX below shows the activity of the *Candida antarctica* lipase that is measured by using 2-hydroxy-4-p-nitrophenyl-butyl-decanoate and para-nitrophenylbutyrate. The activities are expressed in %. The enzymatic reactions were incubated at 60° C. for 40 minutes at pH 3, 4, 5, 6.5, 7 and 8. A negative control without enzyme was also carried out by using the same experimental conditions.

TABLE IX

| pH | 2-Hydroxy-4-p-nitrophenyl-butyl-decanoate | | p-Nitrophenylbutyrate | |
| --- | --- | --- | --- | --- |
| | Lipase B | Without enzyme | Lipase B | Without enzyme |
| 3 | 58.9 | 3.9 | 94.2 | 54.9 |
| 4 | 80.9 | 2.7 | 73 | 63.6 |
| 5 | 96.1 | 2.6 | 100 | 65.6 |
| 6.5 | 100 | 2.9 | 79.5 | 69.2 |
| 7 | 72 | 3.4 | 60.8 | 51.4 |
| 8 | 40 | 2.8 | 103.9 | 103.9 |

VI. Detection of the Release of a Volatile Compound

The first tests were conducted with three different substrates: benzaldehyde, the volatile form, and hydrobenzoin and 1,2-pentanediol, the vicinal forms.

10 mg of each product is mixed with 10 mg of NaIO4 and 1 g of MgSO4, then is left just in air on a shelf.

The detection of aromas is carried out from time to time by sampling a little powder and by adding water. The results that correspond to the observations relative to the perception of perfumes are summarized in Table X below.

TABLE X

| Period | Benzaldehyde | Hydrobenzoin | 1,2-Pentanediol |
| --- | --- | --- | --- |
| 1 day | Strong odor | A simple stirring of the solid with ultrasound is sufficient to release a perceptible odor | A simple stirring of the solid with ultrasound is sufficient to release a perceptible odor |
| 5 days | No more odor | 2 or 3 drops of water should be added to several milligrams of solid | 2 or 3 drops of water should be added to several milligrams of solid |
| 1 month | idem | 2 or 3 ml of water should be added to several milligrams of solid | 2 or 3 ml of water should be added to several milligrams of solid |
| 5 months | idem | idem | A larger amount of solid is necessary |

The detection of the "almond" odor of benzaldehyde, the volatile form, is stable for at least one day. By contrast, thanks to the process of the invention, the oxidation of the vicinal diols corresponding to benzaldehyde makes it possible to spray the "almond" odor of benzaldehyde for several months.

Annex

TABLE XI

| List of Substrates by Functional Groups |
| --- |
| Diols, Amino Alcohols and Azido-alcohol |

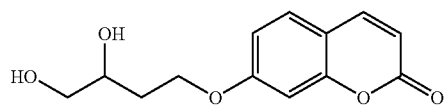 [SMILES: O=c1ccc2ccc(OCCC(O)CO)cc2o1]

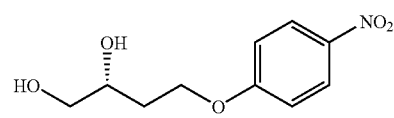 [SMILES: O=[N+]([O-])c1ccc(OCC[C@@H](O)CO)cc1]

TABLE XI-continued
List of Substrates by Functional Groups
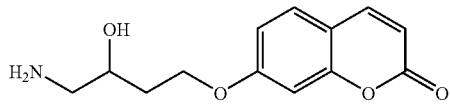 [SMILES: NCC(O)CCOc1ccc2ccc(=O)oc2c1]
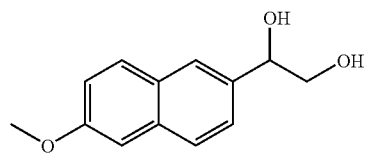 [SMILES: COc1ccc2cc(C(O)CO)ccc2c1]
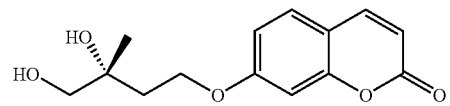 [SMILES: C[C@](O)(CO)CCOc1ccc2ccc(=O)oc2c1]
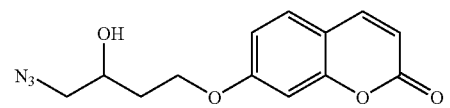 [SMILES: [N-]=[N+]=NCC(O)CCOc1ccc2ccc(=O)oc2c1]
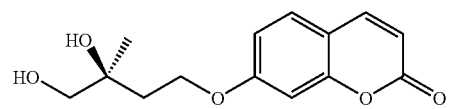 [SMILES: C[C@@](O)(CO)CCOc1ccc2ccc(=O)oc2c1]
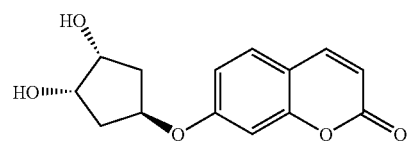 [SMILES: O=c1ccc2ccc(O[C@@H]3C[C@@H](O)[C@@H](O)C3)cc2o1]
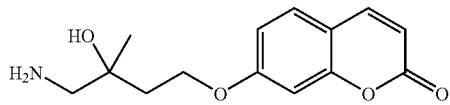 [SMILES: CC(O)(CN)CCOc1ccc2ccc(=O)oc2c1]
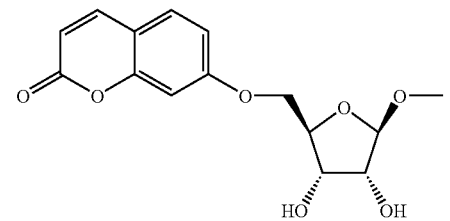 [SMILES: CO[C@@H]1O[C@H](COc2ccc3ccc(=O)oc3c2)[C@@H](O)[C@H]1O]
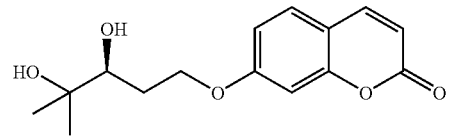 [SMILES: CC(C)(O)[C@@H](O)CCOc1ccc2ccc(=O)oc2c1]
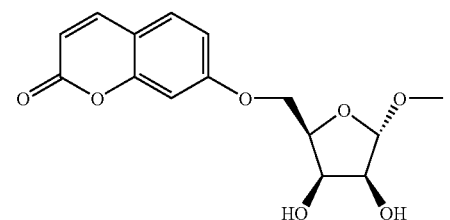 [SMILES: CO[C@H]1O[C@H](COc2ccc3ccc(=O)oc3c2)[C@H](O)[C@@H]1O]

TABLE XI-continued
List of Substrates by Functional Groups
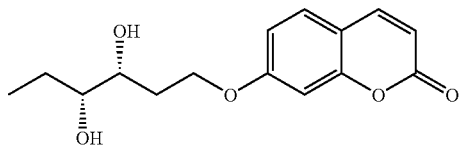 [SMILES: CC[C@@H](O)[C@H](O)CCOc1ccc2ccc(=O)oc2c1]
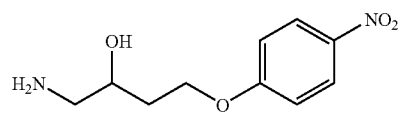 [SMILES: NCC(O)CCOc1ccc([N+](=O)[O-])cc1]
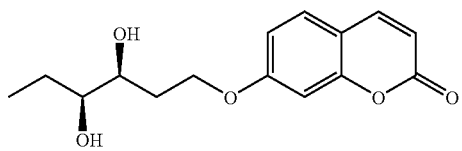 [SMILES: CC[C@H](O)[C@@H](O)CCOc1ccc2ccc(=O)oc2c1]
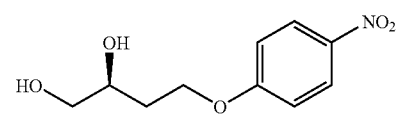 [SMILES: O=[N+]([O-])c1ccc(OCC[C@H](O)CO)cc1]
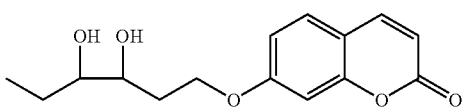 [SMILES: CCC(O)C(O)CCOc1ccc2ccc(=O)oc2c1]
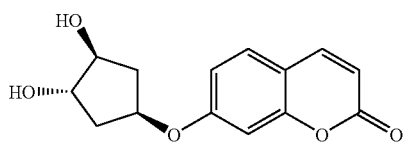
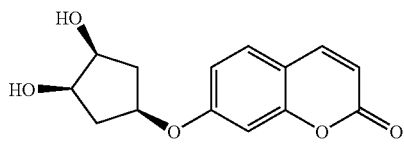 [SMILES: O=c1ccc2ccc(O[C@H]3C[C@@H](O)[C@@H](O)C3)cc2o1]
Esters
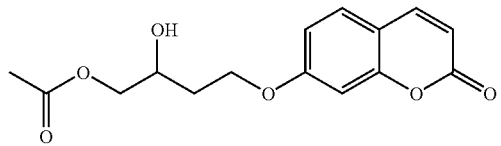 [SMILES: CC(=O)OCC(O)CCOc1ccc2ccc(=O)oc2c1]
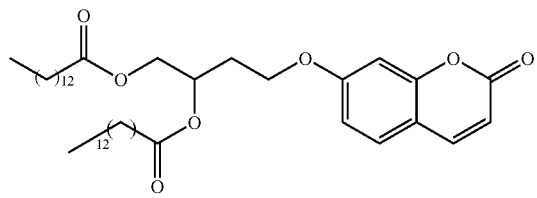
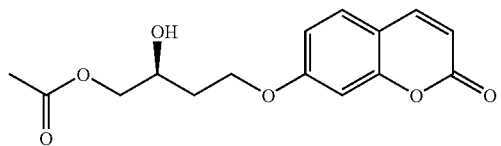 [SMILES: CC(=O)OC[C@@H](O)CCOc1ccc2ccc(=O)oc2c1]

TABLE XI-continued
List of Substrates by Functional Groups
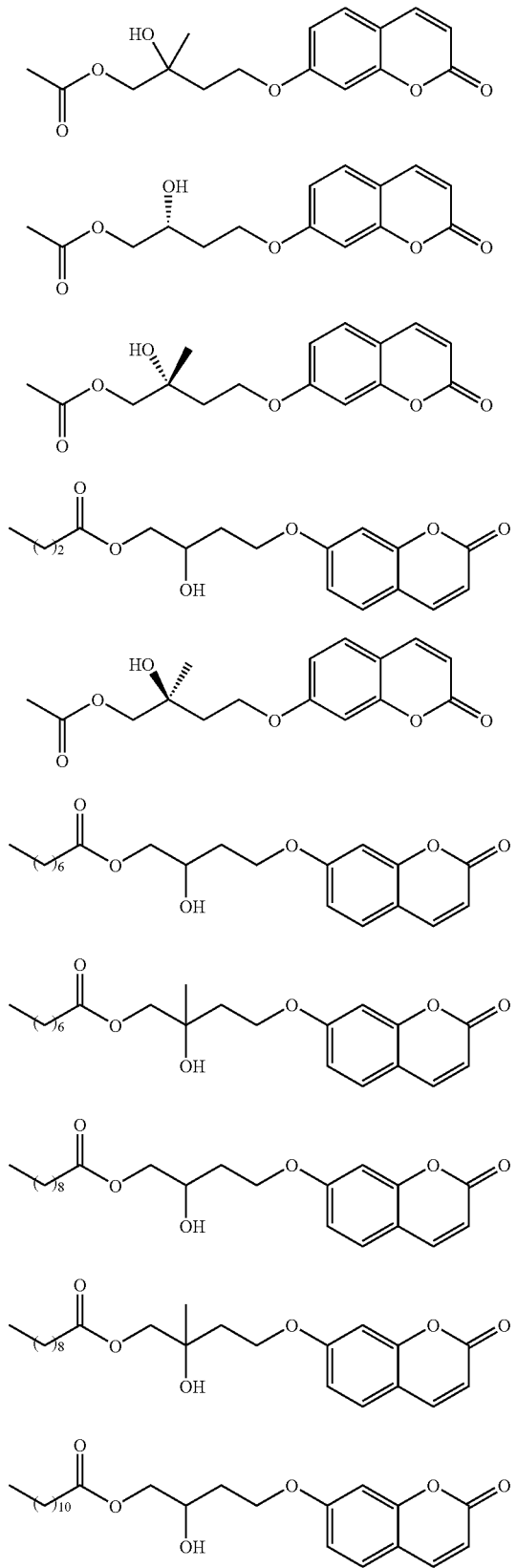

TABLE XI-continued
List of Substrates by Functional Groups
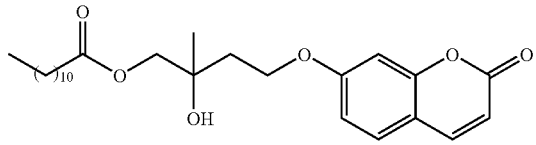
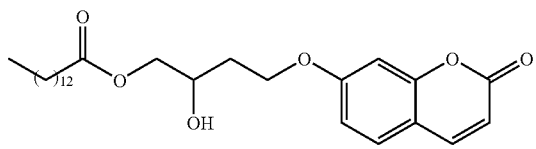
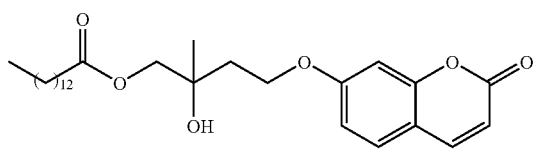
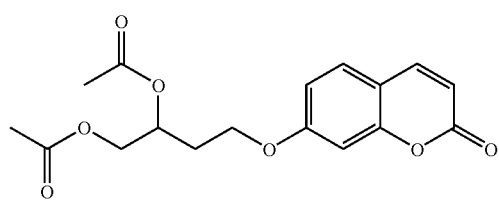 [SMILES: CC(=O)OCC(CCOc1ccc2ccc(=O)oc2c1)OC(C)=O]
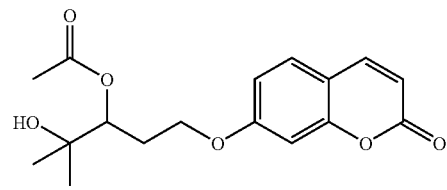 [SMILES: CC(=O)OC(CCOc1ccc2ccc(=O)oc2c1)C(C)(C)O]
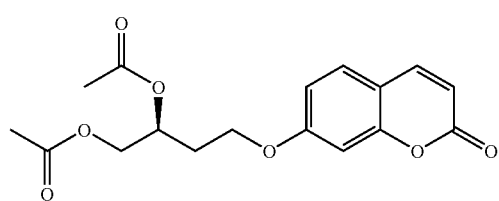 [SMILES: CC(=O)OC[C@H](CCOc1ccc2ccc(=O)oc2c1)OC(C)=O]
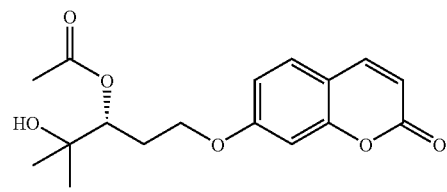 [SMILES: CC(=O)O[C@H](CCOc1ccc2ccc(=O)oc2c1)C(C)(C)O]
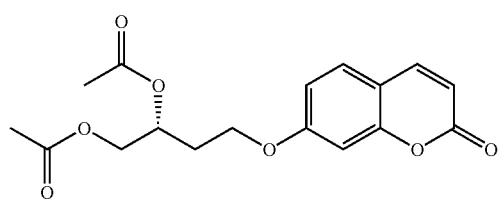

TABLE XI-continued
List of Substrates by Functional Groups
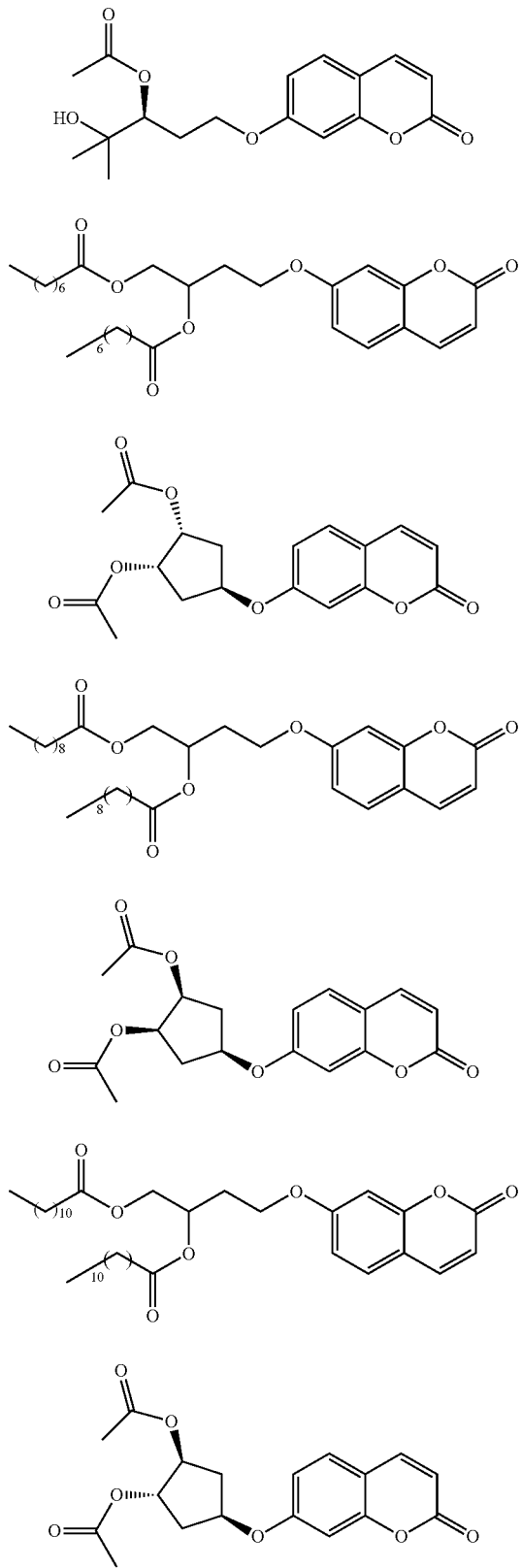

TABLE XI-continued
List of Substrates by Functional Groups
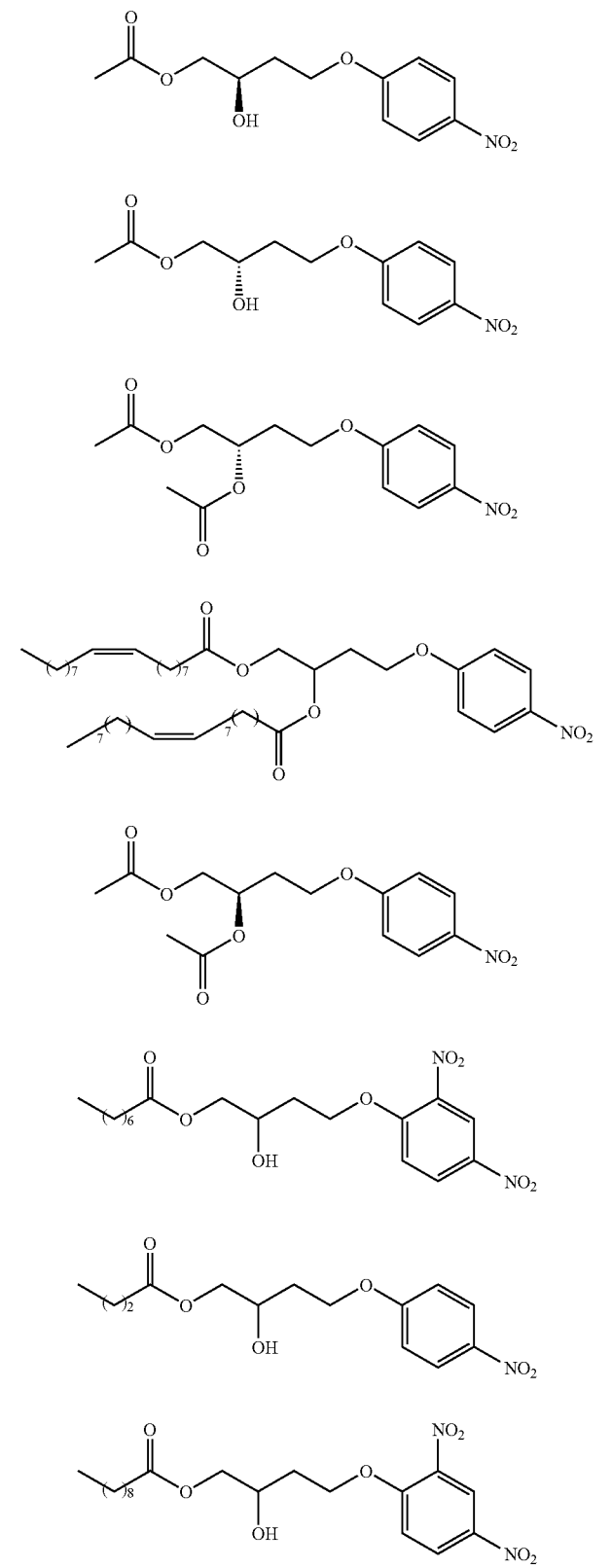

TABLE XI-continued
List of Substrates by Functional Groups
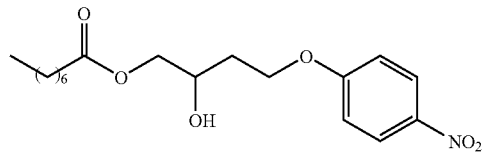
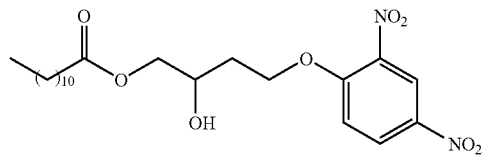
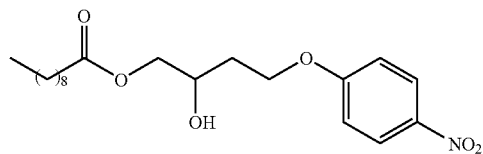
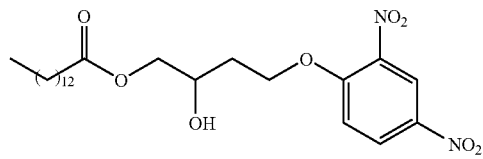
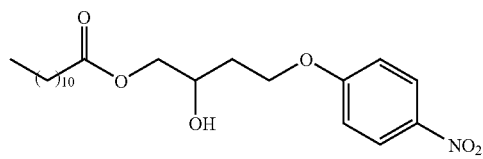
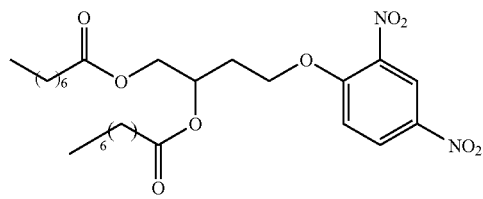
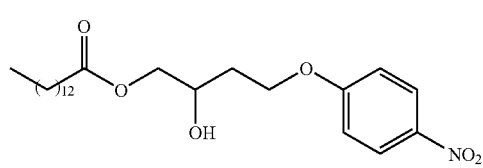
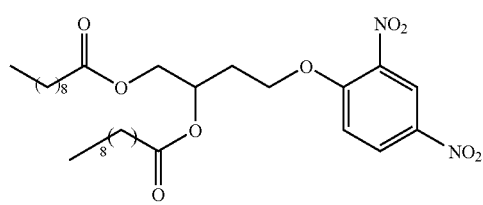
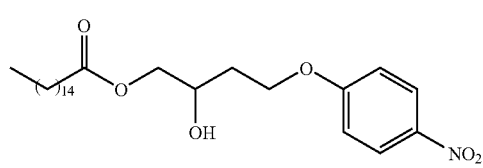

TABLE XI-continued
List of Substrates by Functional Groups
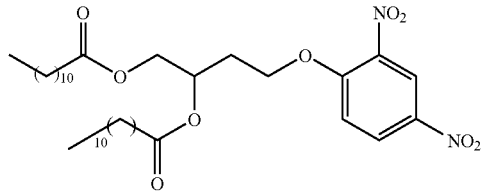
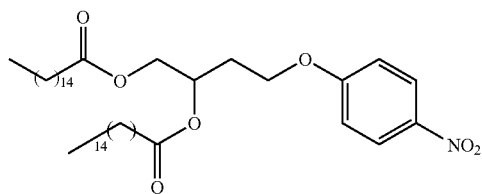
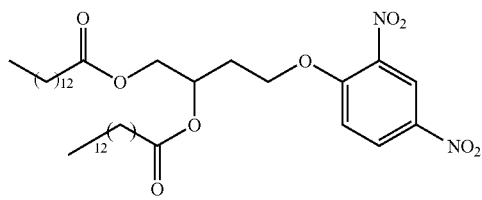
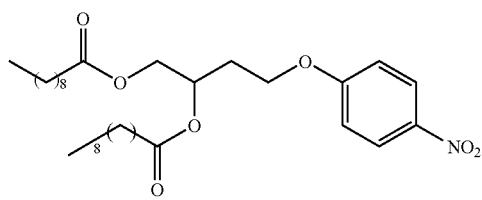
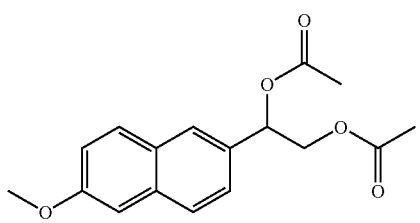 [SMILES: COc1ccc2cc(C(COC(C)=O)OC(C)=O)ccc2c1]
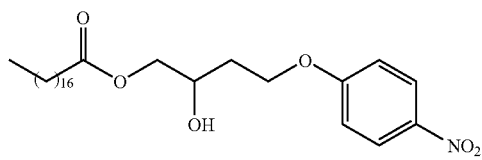
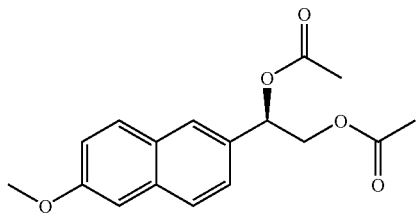 [SMILES: COc1ccc2cc([C@H](COC(C)=O)OC(C)=O)ccc2c1]

TABLE XI-continued
List of Substrates by Functional Groups
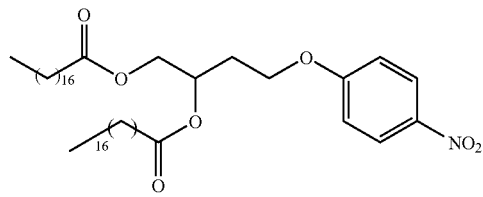
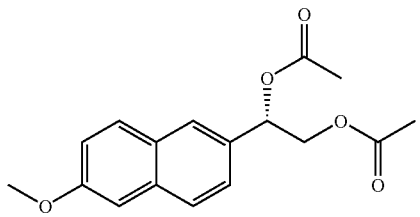
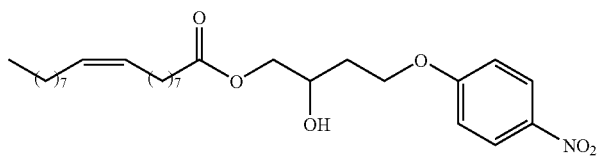
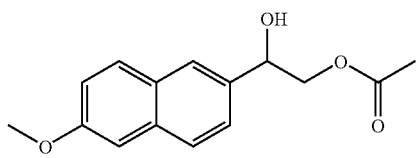 [SMILES: COc1ccc2cc(C(O)COC(C)=O)ccc2c1]
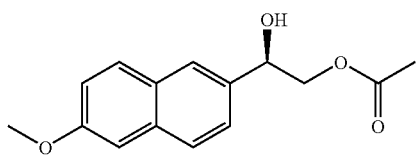 [SMILES: COc1ccc2cc([C@@H](O)COC(C)=O)ccc2c1]
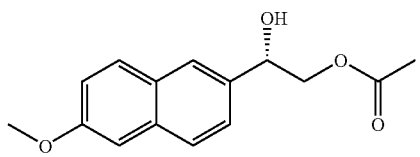
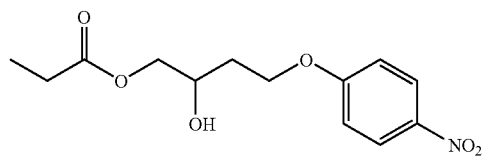
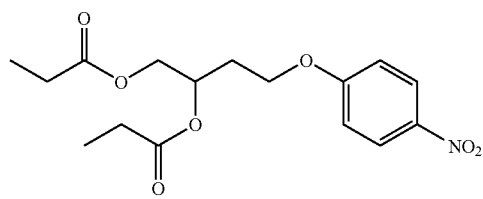 [SMILES: CCC(=O)OCC(CCOc1ccc([N+](=O)[O-])cc1)OC(=O)CC]

TABLE XI-continued
List of Substrates by Functional Groups
Amides
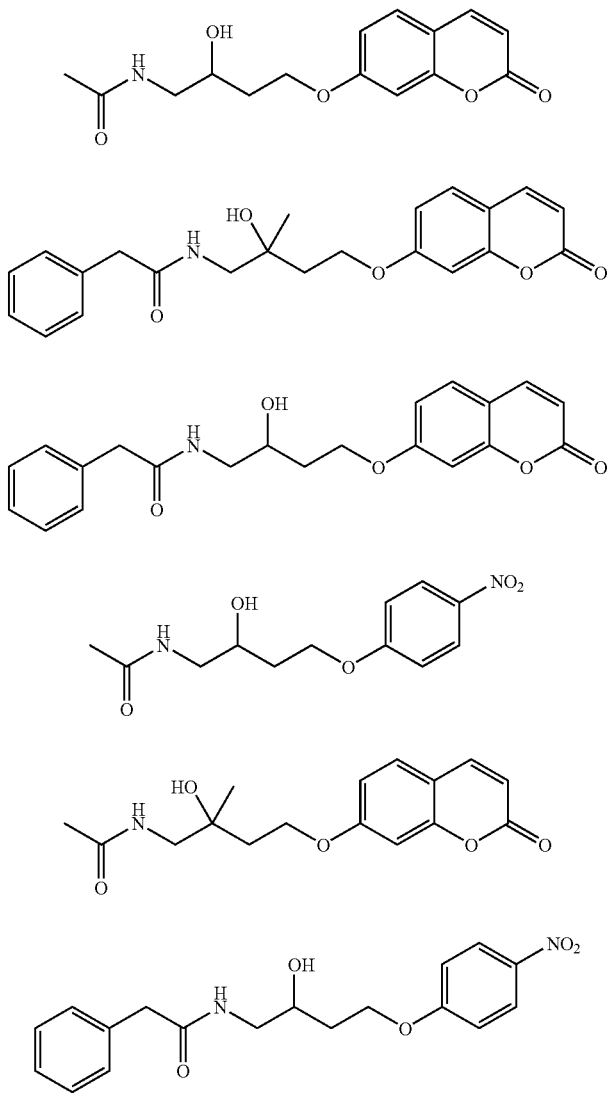
Alcohols
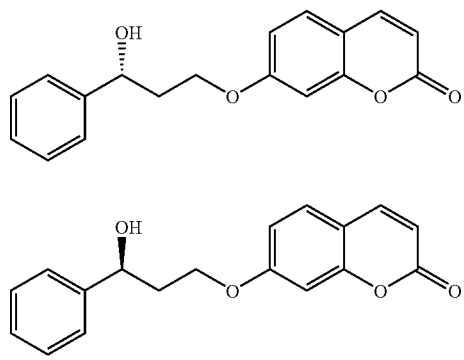

TABLE XI-continued
List of Substrates by Functional Groups
Phosphates
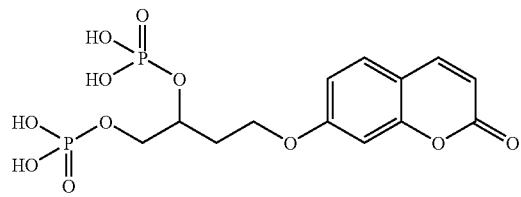 [SMILES: O=c1ccc2ccc(OCCC(COP(=O)(O)O)OP(=O)(O)O)cc2o1]
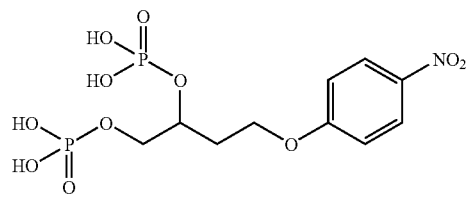 [SMILES: O=[N+]([O-])c1ccc(OCCC(COP(=O)(O)O)OP(=O)(O)O)cc1]
Triols and Derivatives
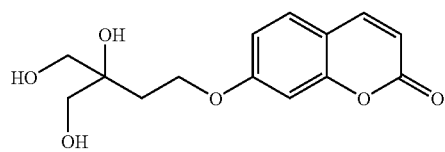 [SMILES: O=c1ccc2ccc(OCCC(O)(CO)CO)cc2o1]
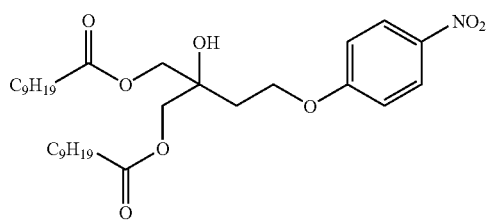
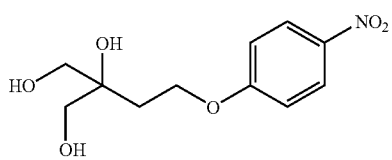 [SMILES: O=[N+]([O-])c1ccc(OCCC(O)(CO)CO)cc1]
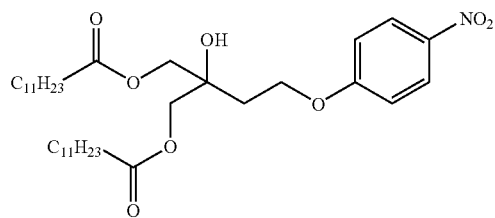
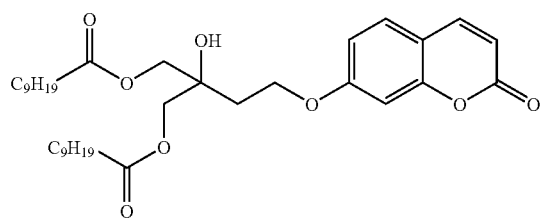

TABLE XI-continued
List of Substrates by Functional Groups
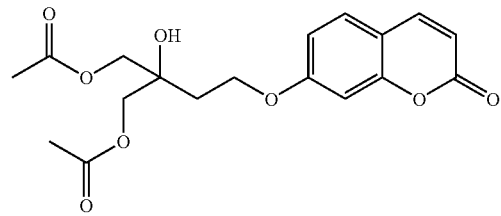 [SMILES: CC(=O)OCC(O)(CCOc1ccc2ccc(=O)oc2c1)COC(C)=O]
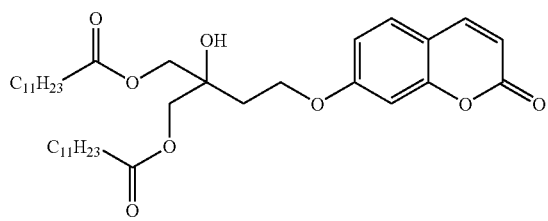
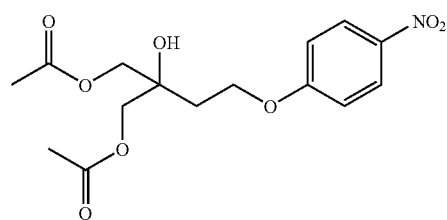 [SMILES: CC(=O)OCC(O)(CCOc1ccc([N+](=O)[O-])cc1)COC(C)=O]
Epoxides
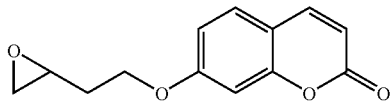 [SMILES: O=c1ccc2ccc(OCCC3CO3)cc2o1]
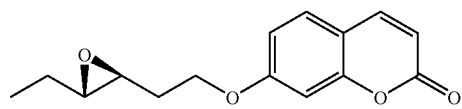 [SMILES: CC[C@@H]1O[C@H]1CCOc1ccc2ccc(=O)oc2c1]
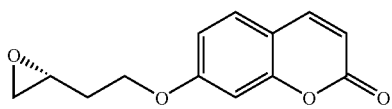 [SMILES: O=c1ccc2ccc(OCC[C@@H]3CO3)cc2o1]
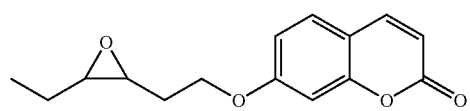 [SMILES: CCC1OC1CCOc1ccc2ccc(=O)oc2c1]
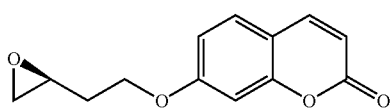 [SMILES: O=c1ccc2ccc(OCC[C@H]3CO3)cc2o1]
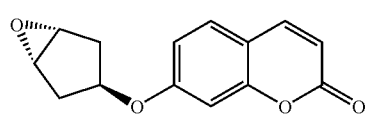 [SMILES: O=c1ccc2ccc(O[C@H]3C[C@@H]4O[C@@H]4C3)cc2o1]
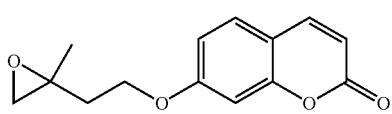 [SMILES: CC1(CCOc2ccc3ccc(=O)oc3c2)CO1]

TABLE XI-continued
List of Substrates by Functional Groups
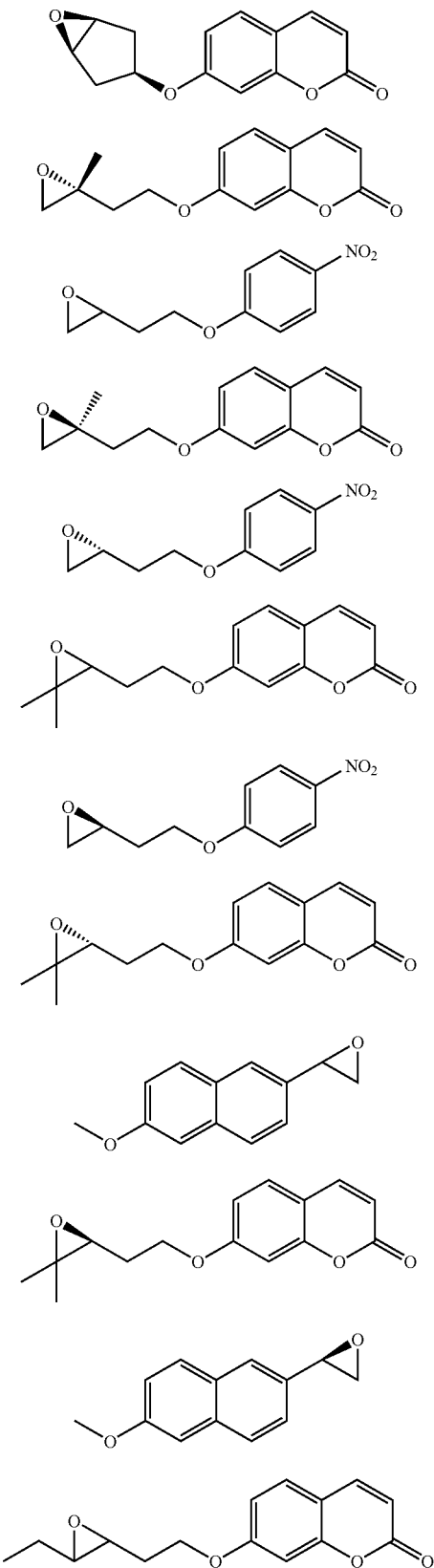

TABLE XI-continued
List of Substrates by Functional Groups
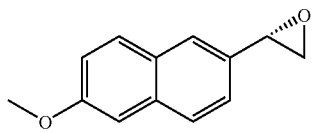
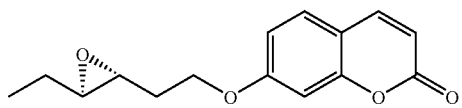 [SMILES: CC[C@H]1O[C@@H]1CCOc1ccc2ccc(=O)oc2c1]
Carbonates
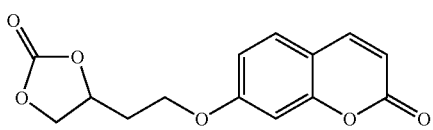 [SMILES: O=C1OCC(CCOc2ccc3ccc(=O)oc3c2)O1]
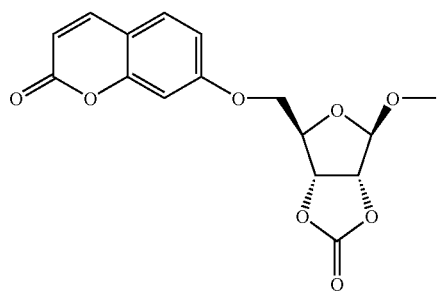 [SMILES: CO[C@@H]1O[C@H](COc2ccc3ccc(=O)oc3c2)[C@H]2OC(=O)O[C@@H]12]
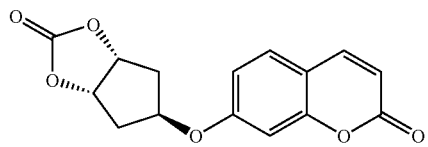 [SMILES: O=C1O[C@H]2C[C@H](Oc3ccc4ccc(=O)oc4c3)C[C@H]2O1]
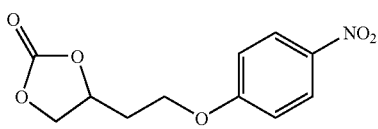 [SMILES: O=C1OCC(CCOc2ccc([N+](=O)[O-])cc2)O1]
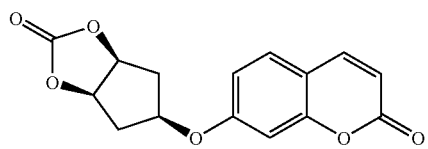 [SMILES: O=C1O[C@H]2C[C@@H](Oc3ccc4ccc(=O)oc4c3)C[C@H]2O1]
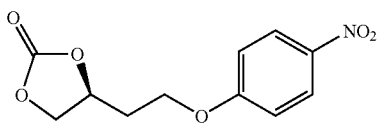 [SMILES: O=C1OC[C@H](CCOc2ccc([N+](=O)[O-])cc2)O1]
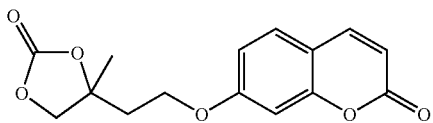 [SMILES: CC1(CCOc2ccc3ccc(=O)oc3c2)COC(=O)O1]

TABLE XI-continued

List of Substrates by Functional Groups

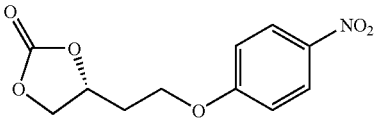 [SMILES: O=C1OC[C@@H](CCOc2ccc([N+](=O)[O-])cc2)O1]
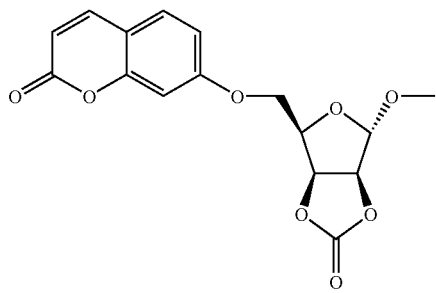 [SMILES: CO[C@H]1O[C@H](COc2ccc3ccc(=O)oc3c2)[C@@H]2OC(=O)O[C@H]12]

What is claimed is:

1. A method for determining the presence of an enzyme comprising:
   (a) contacting a biological sample, suspected of containing the enzyme, with a substrate of -formula (V):

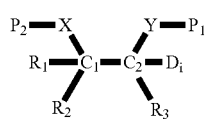

reacting the compound of formula (V) with said enzyme, if present, to give a product of the formula (X)

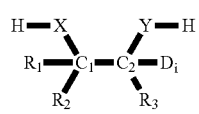

wherein Di is a fragment having a spectrometric property which property is altered upon cleavage of the $C_1$-$C_2$ bond; and
   wherein in the compounds of the formulae (V) and (X):
   (i) $R_1$ to $R_3$, which are identical or different, are H, a substituted or unsubstituted alkyl group, or Di, or $R_1$ together with Di forms a five-membered aliphatic cycle, or $R_2$, together with $C_1$, $C_2$, and Di, forms a cyclic moiety in said substrate;
   (ii) X and Y, which are identical or different, are O, S, or —NH; and
   (iii) $P_1$ and $P_2$, which are identical or different, are a hydrogen atom, an acyl group that is substituted by an aryl, alkyl or peptidyl group; a phosphate group; a phosphate ester group; a phosphonate group; a carbamyl group that is substituted by an aryl, acyl or peptidyl group; a glycosyl group; or a sulfate group, provided that not more than one of the groups $P_1$ and $P_2$ is a hydrogen atom;
   (b) oxidizing the compound of formula (X) with an oxidizing chemical agent, thereby cleaving the bond $C_1$-$C_2$ to obtain a product of formula (D)

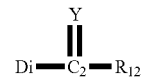

wherein Di, Y and $R_3$ are as defined above; and
   (c) spectrometrically determining the presence of the enzyme by observing the alteration of the spectrometric property of Di.

2. The method according to claim 1, wherein steps (a) and (b) do not occur simultaneously.

3. The method according to claim 1, wherein steps (a) and (b) occur simultaneously, and wherein one or more of groups $R_1$ to $R_3$ are not oxidized by the step (b) oxidation.

4. The method according to claim 1, wherein groups $R_1$ to $R_3$ are stable in a reaction medium comprising an aqueous medium, an organic medium, a two-phase medium, or a solid medium.

5. The method according to claim 1, wherein at least one of steps (a) and (b) are carried out in a reaction medium comprising an aqueous medium, an organic medium, a two-phase medium, or a solid medium.

6. The method according to claim 1, wherein said substrate comprises one or more chiral centers.

7. The method according to claim 1, wherein the oxidation reaction is carried out in an organic medium.

8. The method according to claim 1, wherein the product of formula (D) comprises an aromatic ketone, an aldehyde, or a pheromone.

9. The method according to claim 1, wherein the chemical oxidation of the substrate of formula (V) is followed by a beta-elimination reaction and produces the product of formula (D).

10. The method according to claim 9, wherein the product of formula (D) is a derivative of an aromatic alcohol, a heteroaromatic alcohol, a heteroaromatic amine, a halogen atom, or a phosphoric ester.

11. The method of claim 10, wherein the product of formula (D) comprises fluorescein, phenolphthalein, phenol red, p-nitrophenol, o-nitrophenol, 2,4-dinitrophenol, 6-hydroxynaphthoic acid, 8-hydroxy-pyrene 1,3,6-trisulfonic acid, tyrosine, luciferin, 5-bromo-4-chloro-indolyl, indolyl, quinolinium, nitro-anilinium or pyridoxamine.

12. The method according to claim 1, wherein $R_1$ or $R_2$ is Di and wherein each Di interacts with the other to produce a detectable spectral property.

13. The method according to claim 1, wherein the degree of specificity of the substrate of formula (V) is provided by the structure of any one or more $R_1$-$R_3$.

14. The method according to claim 1, wherein the substrate comprises a cycle comprising $C_1$, $C_2$, $R_2$, and Di.

15. The method of claim 1, wherein the oxidizing chemical agent comprises $H_5IO_6$, $RuO_2$, $OsO_4$, $(CH_3CH_2CH_2)_4N(RuO_4)$, $NaClO_4$, $NaIO_4$, $Na_3H_2IO_6$, $NaMnO_4$, $K_2OsO_4$, $KIO_4$, $KMnO_4$, $KRuO_4$, $K_2RuO_4$, LiOCl, lead acetate, tetrapropylammonium periodate, chromic acid or salts of the latter, $NaBiO_3$, $Ph_3BiCO_3$, $Ca(OCl)_2$, the reagents Ce(IV), Cr(VI), the salts of Co(II), IOAc, I(OAc)$_3$, N-iodosuccinimide, VO(OAc), Pb(OAc)$_4$, $MnO_2$, $H_2O_2$, $Na_2WO_4$, $H_3PO_4$, or mixtures thereof.

16. A method for determining the presence of an enzyme comprising:
 (a) contacting a biological sample, suspected of containing the enzyme, with a substrate of formula (V')

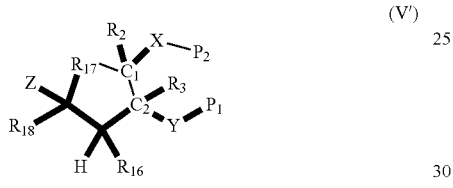

reacting the compound of formula (V) or (V') with said enzyme, if present, to give a product of the formula (X'):

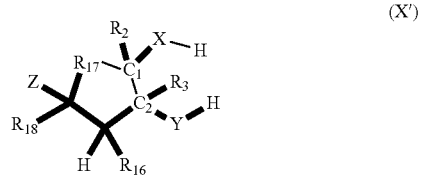

and wherein in the compounds of the formula (X'):

(i) Z is a fragment having a spectrometric property which property is altered upon cleavage of the $C_1$-$C_2$ bond;
 (ii) $R_{17}$ is a substituted or unsubstituted alkyl group;
 (iii) $R_{16}$ and $R_{18}$, which are identical or different, are H, a substituted or unsubstituted alkyl group;
 (iv) X and Y, which are identical or different, are O, S, or —NH; and
 (v) $P_1$ and $P_2$, which are identical or different, are a hydrogen atom, an acyl group that is substituted by an aryl, alkyl or peptidyl group; a phosphate group; a phosphate ester group; a phosphonate group; a carbamyl group that is substituted by an aryl, acyl or peptidyl group; a glycosyl group; or a sulfate group, provided that not more than one of the groups $P_1$ and $P_2$ is a hydrogen atom;

(b) oxidizing the compound of formula (X') with an oxidizing chemical agent, thereby cleaving the bond $C_1$-$C_2$ to obtain a product of formula (D')

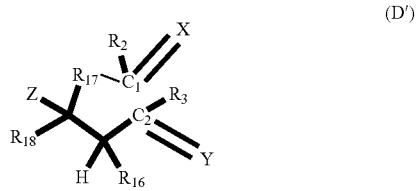

wherein Z, X, Y, $R_2$, $R_3$, $R_{16}$, $R_{17}$, and $R_{18}$ are as defined above; and (c) spectrometrically determining the presence of the enzyme by observing the alteration of the spectrometric property of Z.

17. The method according to claim 16, wherein the chemical oxidation of the substrate of formula (V') is followed by a beta-elimination reaction and produces the product of formula (D').

* * * * *